United States Patent [19]
Haskill et al.

[11] Patent Number: 5,932,537
[45] Date of Patent: Aug. 3, 1999

[54] METHOD FOR ATTENUATING A CELLULAR RESPONSE TO IL-1

[75] Inventors: John S. Haskill, Chapel Hill, N.C.; Peter Ralph, Orinda, Calif.; Joanna Mizen Watson, Chapel Hill, N.C.

[73] Assignee: Chiron Corporation, Emeryville, Calif.

[21] Appl. No.: 08/479,140

[22] Filed: Jun. 7, 1995

Related U.S. Application Data

[63] Continuation-in-part of application No. 08/425,232, Apr. 18, 1995, which is a continuation of application No. 07/791,474, Nov. 8, 1991, abandoned, which is a continuation-in-part of application No. 07/594,827, Oct. 9, 1990, abandoned.

[51] Int. Cl.$^6$ .......................... A61K 45/05; A61K 38/20
[52] U.S. Cl. ................................... 514/2; 514/8; 514/12; 514/21; 424/85.1; 424/85.2
[58] Field of Search .............................. 514/2, 8, 12, 21; 424/85.1, 85.2

[56] References Cited

U.S. PATENT DOCUMENTS

| | | |
|---|---|---|
| 5,011,778 | 4/1991 | Newman et al. . |
| 5,075,222 | 12/1991 | Hannum et al. . |
| 5,180,812 | 1/1993 | Dower et al. . |
| 5,359,032 | 10/1994 | Dayer et al. . |
| 5,455,330 | 10/1995 | Haskill et al. . |

FOREIGN PATENT DOCUMENTS

WO 89/11540  11/1989  WIPO .

OTHER PUBLICATIONS

Carter, et al., "Purification, cloning, expression and biological characterization of an interleukin-1 receptor antagonist protein," *Nature* 344:633–638 (Apr. 12, 1990).

Cominelli, et al., "Interleukin 1 (IL–1) Gene Expression, Synthesis, and Effect of Specific IL–1 Receptor Blockade in Rabbit Immune Complex Colitis," *J. Clin. Invest.*, 86:972–980 (Sep. 1990).

Dinarello, et al., "Multiple Biological Activities of Human Recombinant Interleukin 1, " *J. Clin. Invest.*, 77:1734–1739 (Jun. 1986).

Eisenberg, et al., "Primary structure and functional expression from complementary DNA of a human interleukin–1 receptor antagonist," *Nature*, 343:341–346, (Jan. 25, 1990).

Fanslow, et al., "Regulation of Alloreactivity in Vivo by a Soluble Form of the Interleukin–1 Receptor, " *Science*, 248:739–742, (May 1990).

Gosset, et al., "Production of an Interleukin–1 Inhibitor Factor by Human Alveolar Macrophages from Normals and Allergic Asthmatic Patients," *Am. Rev. Respir. Dis.*, 138:40–46 (1988).

Gershenwald, et al., "Interleukin 1 receptor blockade attenuates the host inflammatory response," *Proc. Natl. Acad. Sci. USA*, 87:4966–4970 (Jul. 1990).

Hannum, et al., "Interleukin–1 receptor antagonist activity of a human interleukin–1 inhibitor," *Nature*, 343:336–339 (Jan. 25, 1990).

Maliszewski, et al., "Cytokine Receptors and B Cell Functions—1. Recombinant Soluble Receptors Specifically Inhibit IL–1– and IL–4–Induced B Cell Activities in Vitro, " *The Journal of Immunology*, 144:3028–3033, No. 8 (Apr. 15, 1990).

Oppenheim, et al., "There is More Than One Interleukin 1," *Immunology Today, Reviews*, 7:45–56 No. 2 (1986).

Palaszynski, "Synthetic C–Terminal Peptide of IL–1 functions as a Binding Domain As Well As An Antagonist For The IL–1 Receptor," *Biochemical and Biophysical Research Communications*, 147:204–211, No. 1 (Aug. 31, 1987).

Seckinger, et al., "A Urine Inhibitor of Interleukin 1 Activity Affects Both Interleukin 1α and 1β But Not Tumor Necrosis Factor α," *The Journal of Immunology*, 139:1541–1545, No. 5 (Sep. 1, 1987).

Simpson, et al., "Reduction of Experimental Canine Myocardial Reperfusion Injury by a Monoclonal Antibody (Anti– Mol, Anti–CD11b) That Inhibits Leukocyte Adhesion," *J. Clin. Invest.*, 81:624–629 (Feb. 1988).

Dorland's Illustrated Medical Dictionary, 24th Ed., W.B. Saunders Company, Philadelphia, PA., p. 760, defining "ischemia," (1965).

Vedder, et al., "A Monoclonal Antibody to he Adherence–promoting Leukocyte Glycoprotein, CD18, Reduces Organ Injury and Improves Survival from Hemorrhagic Shock and Resuscitation in Rabbits," *J. Clin. Invest.*, 81:939–944 (1988).

Cotran, et al., "Induction and Detection of a Human Endothelial Activation Antigen In Vivo," Brief Definitive Report, *J. Exp. Med.* 164: 661–666, (Aug. 1986).

Buchan, et al., "Interleukin–1 and tumor necrosis factor mRNA expression in rheumatoid arthritis: prolonged production of IL–1α," *Clin. Exp. Immunol.* 73:449–455 (Mar. 1988).

*Primary Examiner*—Garnette D. Draper
*Attorney, Agent, or Firm*—Donald J. Pochopien; Paul B. Savereide; Robert P. Blackburn

[57] ABSTRACT

Medicaments and methods of using the same are disclosed for treating or preventing diseases resulting from undesirable cell adhesion of IL-1 receptor positive cells to biological materials, particular to endothelial cells, or autoimmune related diseases, preferably graft versus host disease, or IL-1 dependent cancers.

10 Claims, 10 Drawing Sheets

```
AGCTCCACCCTGGGAGGGACTGTGGCCCAGGTACTGCCCGGGTGCTACTT                    -71

TATGGGCAGCAGCTCAGTTGAGTTAGAGTCTGGAAGACCTCAGA.AGACC                    -22

MetAlaLeuGluThrIleCysArgPro
TCCTGTCCTATGAGGCCCTCCCCATGGCTTTAGAGACGATCTGCCGACCC                     27

63
SerGlyArgLysSerSerLysMetGlnAlaPheArgIleTryAspValAs
TCTGGGAGAAAATCCAGCAAGATGCAAGCCTTCAGAATCTGGGATGTTAA                     77 nGlnLysThrPheTyrLeuArgAsnAsnGlnLeuValAlaGlyTyrLeuG
CCAGAAGACCTTCTATCTGAGGAACAACCAACTAGTTGCTGGATACTTGC                    127 lnGlyProAsnValAsnLeuGluGluLysIleAspValValProIleGlu
AAGGACCAAATGTCAATTTAGAAGAAAAGATAGATGTGGTACCCATTGAG                    177

ProHisAlaLeuPheLeuGlyIleHisGlyGlyLysMetCysLeuSerCy
CCTCATGCTCTGTTCTTGGGAATCCATGGAGGGAAGATGTGCCTGTCCTG                    227 sValLysSerGlyAspGluThrArgLeuGlnLeuGluAlaValAsnIleT
TGTCAAGTCTGGTGATGAGACCAGACTCCAGCTGGAGGCAGTTAACATCA                    277 hrAspLeuSerGluAsnArgLysGlnAspLysArgPheAlaPheIleArg
CTGACCTGAGCGAGAACAGAAAGCAGGACAAGCGCTTCGCCTTCATCCGC                    327

SerAspSerGlyProThrThrSerPheGluSerAlaAlaCysProGlyTr
TCAGACAGTGGCCCCACCACCAGTTTTGAGTCTGCCGCCTGCCCCGGTTG                    377 pPheLeuCysThrAlaMetGluAlaAspGlnProValSerLeuThrAsnM
GTTCCTCTGCACAGCGATGGAAGCTGACCAGCCCGTCAGCCTCACCAATA                    427 etProAspGluGlyValMetValThrLysPheTyrPheGlnGluAspGlu
TGCCTGACGAAGGCGTCATGGTCACCAAATTCTACTTCCAGGAGGACGAG                    477

TAG                                                                   480
```

FIG. 1

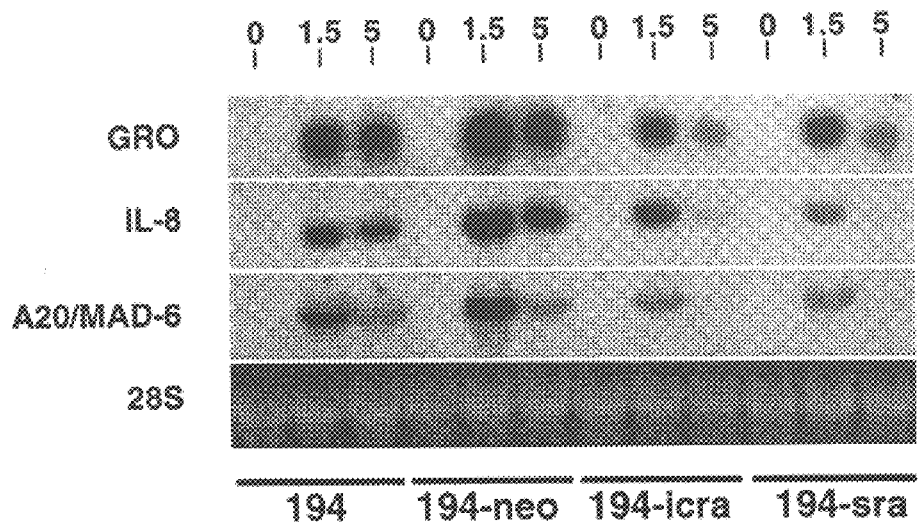
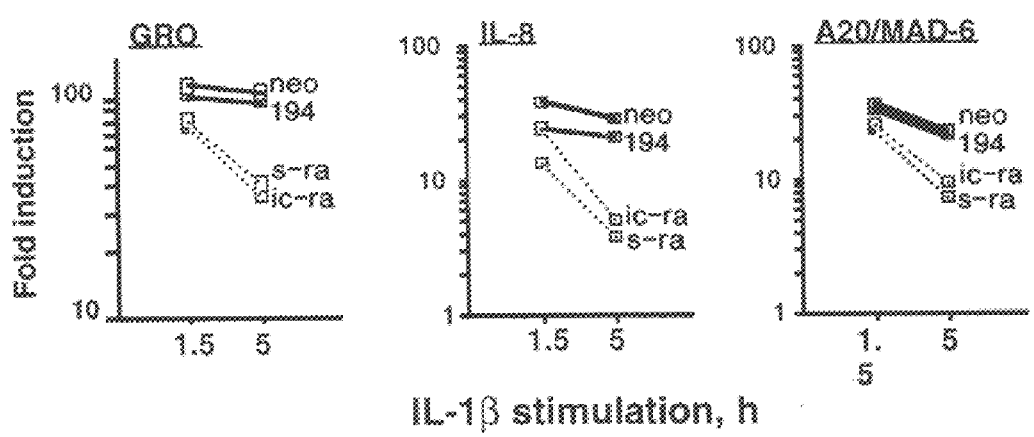
FIG. 9C

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 603 base pairs
      (B) TYPE: nucleic acid
      (C) STRANDEDNESS: single
      (D) TOPOLOGY: linear (ii) MOLECULE TYPE: protein (ix) FEATURE:
      (A) NAME/KEY: CDS
      (B) LOCATION: 124..600

(xi) SEQUENCE DESCRIPTION: SEQ ID NO:1:

```
AGCTCCACCC TGGGAGGGAC TGTGGCCCAG GTACTGCCCG GGTGCTACTT TATGGGCAGC      60

AGCTCAGTTG AGTTAGAGTC TGGAAGACCT CAGANAGACC TCCTGTCCTA TGAGGCCCTC     120

CCC ATG GCT TTA GAG ACG ATC TGC CGA CCC TCT GGG AGA AAA TCC AGC      168
    Met Ala Leu Glu Thr Ile Cys Arg Pro Ser Gly Arg Lys Ser Ser
    1               5                  10                 15
```

```
AAG ATG CAA GCC TTC AGA ATC TGG GAT GTT AAC CAG AAG ACC TTC TAT        216
Lys Met Gln Ala Phe Arg Ile Trp Asp Val Asn Gln Lys Thr Phe Tyr
             20                  25                  30

CTG AGG AAC AAC CAA CTA GTT GCT GGA TAC TTG CAA GGA CCA AAT GTC        264
Leu Arg Asn Asn Gln Leu Val Ala Gly Tyr Leu Gln Gly Pro Asn Val
         35                  40                  45

AAT TTA GAA GAA AAG ATA GAT GTG GTA CCC ATT GAG CCT CAT GCT CTG        312
Asn Leu Glu Glu Lys Ile Asp Val Val Pro Ile Glu Pro His Ala Leu
     50                  55                  60

TTC TTG GGA ATC CAT GGA GGG AAG ATG TGC CTG TCC TGT GTC AAG TCT        360
Phe Leu Gly Ile His Gly Gly Lys Met Cys Leu Ser Cys Val Lys Ser
 65                  70                  75

GGT GAT GAG ACC AGA CTC CAG CTG GAG GCA GTT AAC ATC ACT GAC CTG        408
Gly Asp Glu Thr Arg Leu Gln Leu Glu Ala Val Asn Ile Thr Asp Leu
 80                  85                  90                  95

AGC GAG AAC AGA AAG CAG GAC AAG CGC TTC GCC TTC ATC CGC TCA GAC        456
Ser Glu Asn Arg Lys Gln Asp Lys Arg Phe Ala Phe Ile Arg Ser Asp
             100                 105                 110

AGT GGC CCC ACC ACC AGT TTT GAG TCT GCC GCC TGC CCC GGT TGG TTC        504
Ser Gly Pro Thr Thr Ser Phe Glu Ser Ala Ala Cys Pro Gly Trp Phe
         115                 120                 125

CTC TGC ACA GCG ATG GAA GCT GAC CAG CCC GTC AGC CTC ACC AAT ATG        552
Leu Cys Thr Ala Met Glu Ala Asp Gln Pro Val Ser Leu Thr Asn Met
     130                 135                 140

CCT GAC GAA GGC GTC ATG GTC ACC AAA TTC TAC TTC CAG GAG GAC GAG        600
Pro Asp Glu Gly Val Met Val Thr Lys Phe Tyr Phe Gln Glu Asp Glu
 145                 150                 155

TAG                                                                   603

(2) INFORMATION FOR SEQ ID NO:2:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Leu Glu Thr Ile Cys Arg Pro Ser Gly Arg Lys Ser Ser Lys
 1               5                  10                  15

Met Gln Ala Phe Arg Ile Trp Asp Val Asn Gln Lys Thr Phe Tyr Leu
             20                  25                  30

Arg Asn Asn Gln Leu Val Ala Gly Tyr Leu Gln Gly Pro Asn Val Asn
         35                  40                  45

Leu Glu Glu Lys Ile Asp Val Val Pro Ile Glu Pro His Ala Leu Phe
     50                  55                  60

Leu Gly Ile His Gly Gly Lys Met Cys Leu Ser Cys Val Lys Ser Gly
 65                  70                  75                  80

Asp Glu Thr Arg Leu Gln Leu Glu Ala Val Asn Ile Thr Asp Leu Ser
                 85                  90                  95

Glu Asn Arg Lys Gln Asp Lys Arg Phe Ala Phe Ile Arg Ser Asp Ser
             100                 105                 110

Gly Pro Thr Thr Ser Phe Glu Ser Ala Ala Cys Pro Gly Trp Phe Leu
         115                 120                 125

Cys Thr Ala Met Glu Ala Asp Gln Pro Val Ser Leu Thr Asn Met Pro
     130                 135                 140

Asp Glu Gly Val Met Val Thr Lys Phe Tyr Phe Gln Glu Asp Glu
 145                 150                 155
```

METHOD FOR ATTENUATING A CELLULAR RESPONSE TO IL-1

This application is a continuation-in-part of U.S. Ser. No. 08/425,232, filed Apr. 18, 1995, now pending, which is a file wrapper continuation of U.S. Ser. No. 07/791,474, filed Nov. 8, 1991, now abandoned, which is a continuation-in-part of U.S. Ser. No. 07/594,827, filed Oct. 9, 1990, now abandoned.

FIELD OF THE INVENTION

This invention is in the area of medicinal chemistry, and presents medically useful compositions consisting of IL-1 receptor antagonists that have prophylactic or therapeutic applications for treating a variety of diseases including endothelial cell associated diseases, autoimmune related diseases, and cancer.

BACKGROUND OF THE INVENTION

Cytokines are small molecular weight proteins that have a myriad of normal biological functions as well as being associated with various diseases. For example, the cytokines interleukin-1 (IL-1) and tumor necrosis factor (TNF) have been demonstrated to have multiple biological activities with the two prominent being fever production and leukocyte activation. Moreover, both cytokines, alone or in combination, cause a shock state in animals that hemodynamically and hematologically is characteristic of septic shock in man caused by bacterial infection. TNF, in addition, has recently been shown to be involved in initiating the expression of human immunodeficiency virus in human cells that carry latent virus. Folks et al., 1989, *PNAS (USA)*, 86:2365. TNF and IL-1 also play a role in various autoimmune diseases, particularly arthritis. Duff, et al., 1987, *International Conference on Tumor Necrosis Factor and Related Cytotoxins*, 175:10.

Endothelial cell injury, or injury to the vascular system, can occur as a result of a number of disease in which there appears to be cytokine involvement. For example, ischemia-related injury to either cells, tissues or organs is responsible for many significant clinical disorders, including stroke, vascular disease, organ transplantation, and myocardial infarction. Leukocytes, particularly, neutrophils or monocytes, are thought to be the primary causative agent and have been shown to cause extensive vascular tissue damage arising as a result of the release of oxygen-derived free radicals, as well as proteases and phospholipases from the leukocytes at the site of injury. Harlan, J. M., 1987, *Acta. Med. Scand. Suppl.*, 715:123; Weiss, S., 1989, *New England J. of Med.*, 320:365. Cytokines are thought to be chemotactic agents for leukocytes and may be involved in attracting them to the site of tissue injury. Additionally, other studies have shown that cytokines are involved in causing leukocytes to adhere to the vascular endothelial cell layer which sets the stage for the release of noxious chemicals that cause vascular tissue damage.

Further evidence for the role of leukocytes in disease comes from studies which have shown that animals depleted of peripheral blood leukocytes show significantly reduced damage from myocardial ischemia and reperfusion. Further, reperfusion injury can be minimized by in vivo administration of monoclonal antibody to an adhesion protein present on leukocytes, termed MAC-1 (discussed more below). Finally, a rabbit model of hemorrhagic shock and resuscitation reveals that monoclonal antibodies against the β subunit of MAC-1 exhibited a protective effect to liver and the asternal intestinal track. Simpson, et al., 1988, *J. of Clinical Invest.*, 81:624; Vedder, N. and Harlan, J., 1988, *J. of Clinical Invest.*, 81:676.

The foregoing studies suggests significant therapeutic value for reagents that block the adhesion of leukocytes in controlling tissue and organ injury resulting from a number of disease situations including myocardial infarction, hemorrhagic shock, and other events that cause ischemia that are followed by reestablishing normal circulatory blood flow.

The initial event that leads to leukocyte, particularly neutrophil, damage of endothelial cells is the adhesion of neutrophils to the endothelial cell surface. In significant part this is mediated by cellular adhesion molecules associated with the neutrophils that cause them to bind to the endothelial cell surface. The neutrophil adhesion molecules bind to a molecule on the surface of endothelial cells termed ICAM-1 (Intercellular Adhesion Molecule 1). ICAM-1 is induced by one of several cytokines, including IL-1 and TNF. To date, a partial list of the adhesion molecules that have been identified that are involved in this reaction are lymphocyte function-associated antigen-1 (LFA-1), macrophage antigen-1 (MAC-1), also termed MO-1, OKM-1 and complement receptor type-3 (CR-3), and p150,95, also termed complement receptor type-4 (CR-4) and Leu M-5. These molecules collectively have been termed the LFA-1 family, leukocyte adhesion proteins, leuCAM, and the leukocytes integrins. All three molecules are α-β heterodimers. The β subunit is identical in the three molecules, while the α subunit differs. Kurzinger, K., and Springer, T. A., 1982, *J. of Biol. Chem.*, 257:12412; Sanchez-Madrid, F., et al., 1983, *J. Exp. Med.*, 158:1785; Trowbridge, I. S., and Omary, M. B., 1981, *PNAS (USA)*, 78:3039. Studies have shown the common β subunit to play the predominant role in the adhesion-related functions of these molecules. Recently the cDNA clone that encodes the β subunit of human LFA-1, MAC-1, and p150,95 has been isolated. Kishimoto, T., et al., 1987, *Cell*, 48:681; and Law, S. K. A. et al., 1987, *EMBO J.*, 6:915–919.

Studies have implicated the leukocyte integrins in cellular adhesion events. For example, LFA-1 is involved in antigen-dependent and antigen-independent interactions of immune cells. Springer, T. A., et al., 1987, *Annual Review Immun.*, 5:223; Martz, E., 1986, *Hum. Immunology*, 18:3. Most telling are studies utilizing a monoclonal antibody to LFA-1, which have revealed that binding to LFA-1 by monoclonal antibody partially or totally inhibits T lymphocyte adherence to endothelial cells (Mentzer, S. J., et al. 1986, *J. of Cell Physiol.*, 126:285), fibroblasts (Dustin, N. L., et al., 1986, *J. of Immun.*, 137:245), epidermal keratinocytes (Dustin, N. L., et al., 1988, *J. of SubBiology*, 107:321), and hepatocytes (Roos, E., and Roossien, F., 1987, *J. of SubBiology*, 105:553). Additionally, MAC-1 has been shown to be involved in macrophage binding to Leishmania Promastigotes, *E. coli*, and Histoplasma Capsulatum. Mosser, D. and Edelson, P., 1985, *J. of Immun.*, 135:2785; Wright, S. and Jong, M., 1986, *J. of Exp Med.*, 164:1876; Bullock, W. and Wright, S., 1987, *J. of Exp. Med*, 165:195. Other studies have shown that MAC-1 is involved in neutrophil and monocyte chemotaxis, as well as adherence to glass and plastic surfaces, and to endothelial and epithelial cell monolayers. p150,95 is reported to be significantly involved in peripheral blood monocyte adhesion to substrates and endothelial cells, phagocytosis of latex particles, and chemotaxis. Keizer, et al., 1987, *Eur. J. of Immun.*, 17:1317; te Velde, A., et al., 1987, Immunology, 61:261. Further, studies using a monoclonal antibody that is directed to p150,95 have shown it to be utilized in conjugate formation by cytotoxic T lymphocytes.

There are two forms of IL-1: IL-1 α and IL-1 β. Although these molecules share limited sequence homology they have similar biological activity. Dinarello, C. A., et al., 1986, *Journal Clinical Invest.,* 77:1734. Both molecules have molecular weights of about 17.5 kD, and are produced from a precursor molecule with a molecular weight of about 31 kD.

Because IL-1 has pleiotropic biological activities many of which adversely affect the organism, it would be expected that the molecule must be tightly regulated if it is not to be injurious. Indeed, there are several reports of IL-1 inhibitors that regulate the action of IL-1. IL-1 inhibitory activity has been reported in monocyte conditioned medium, wherein the monocytes are grown on adherent immune complexes. Arend, W. P., et al., 1985, *Journal of Immun.,* 134:3868. Additionally, an inhibitor has been reported to be present in urine. Seckinger, P., et al., 1987, *Journal of Immun.,* 139:1546. Lastly, two protein inhibitors, purified and cloned, that have interleukin-1 receptor antagonist activity have been reported. Hannum, et al., 1990, *Nature,* 343:336; Eisenberg, S., et al., 1990, *Nature,* 343:341; and Haskill, S., et al., U.S. Ser. No. 517,276, filed May 1, 1990; Carter, D. et al., 1990, *Nature,* 344:633.

It is thought that the IL-1 inhibitor present in urine, and which has been partially purified and characterized by Seckinger, P. et al., supra and Seckinger, P., et al, 1987, *Journal of Immun.,* 139:1541 is similar, if not identical to the cloned IL-1 receptor antagonist reported by Eisenberg, S., et al., supra; and Carter, D., et al., 1990, *Nature,* 344: 633.

As alluded to above, the leukocyte integrins bind to the cell surface protein, ICAM-1, which in turn is induced by one or more cytokines, particularly IL-1 or TNF. Thus, it will be appreciated that an effective modality for preventing endothelial cell injury that occurs during various diseases would be to interfere with the induction of ICAM-1 via molecules that prevent or interfere with the activity of IL-1, TNF or other molecules that induce ICAM-1.

IL-1 also plays a role in various autoimmune or autoimmune related diseases (Duff, et al., 1987, International Conference on Tumor Necrosis Factor and Related Cytotoxins, 175:10), particularly graft versus host rejection involving bone marrow transplants. This is attributable, at least in part, to IL-1 induction of IL-2 production by T-cells which in turn promotes the growth of additional T-cells. Thus, the graft from a donor contains a significant number of immunocompetent lymphoid cells that can mount an effective destructive reaction against host cells. Bone marrow transplants are often employed to treat various malignant diseases, including leukemia Generally this involves immunologically crippling the leukemic patient, and then transplanting bone marrow from a donor. Unless the lymphoid cells in the donor marrow are suppressed they can react against recipient tissue antigens, often with dire consequences.

A variety of drugs, and antisera to lymphoid cells are used to treat graft versus host disease. Particularly useful drugs are corticosteroids, othiopirne, and cyclosporine. In addition, various monoclonal antibodies, alone or when coupled to a cytotoxic agent are available for ridding the donor marrow of lymphoid cells. P. S. Russell et al., *Annual Review Medicine.,* 35:63 (1984). These drugs, however, have significant untoward side effects.

Finally, it has recently been suggested that IL-1 is an autocrine and paracrine growth factor for particular cancers. Tsai, 1987, *J. Natl. Cancer Inst.,* 79:77. Thus, compounds that interfere with the cancer growth activity of IL-1 may be effective chemotherapeutics.

SUMMARY OF THE INVENTION

The invention presented herein describes applications of medicaments consisting of IL-1 receptor antagonists for preventing or treating diseases, as well as methods for preventing or treating diseases using IL-1 receptor antagonists in appropriate assay formats.

A second aspect of the invention presents applications of medicaments consisting of IL-1 receptor antagonists for preventing or treating diseases caused by the undesirable adhesion of leukocytes to endothelial cells, or for preventing or treating autoimmune related diseases, preferably graft versus host disease, or for treating IL-1 dependent cancers.

A third aspect of the invention presents applications of medicaments consisting of IL-1 receptor antagonists for preventing or treating diseases that result in endothelial cell damage, preferably ischemia-related diseases, including stroke, vascular disease, organ transplantation, and myocardial infarction.

A fourth aspect of the invention is the description of medical uses of intracellular IL-1 receptor antagonists for preventing or treating diseases that result in endothelial cell damage, preferably ischemia-related diseases, including stroke, vascular disease, organ transplantation, and myocardial infarction, or for preventing or treating autoimmune related diseases, preferably graft versus host disease, or for treating IL-1 dependent cancers.

A fifth aspect of the invention is a method of treating or preventing HIV infection in a host consisting of incorporating into host cells a nucleotide sequence that encodes IL-1 receptor antagonist activity.

These and other aspects of the invention will be apparent upon a full consideration of the invention as presented below.

BRIEF DESCRIPTION OF THE DRAWINGS

FIG. 1 discloses a DNA sequence (SEQ ID NO: 1) and corresponding amino acid sequence (SEQ ID NO: 2) of the intracellular IL-1 receptor antagonist encoded thereby.

FIG. 9C shows an RNA blot illustrating the effect of exposure to IL-1β (1 ng/ml for the times indicated) on the expression of GRO, IL-8, and A20/MAD-6 mRNA in ovarian cancer cell lines stably transfected with an icIL-1ra or sIL-1ra expression vector.

Figure 2:
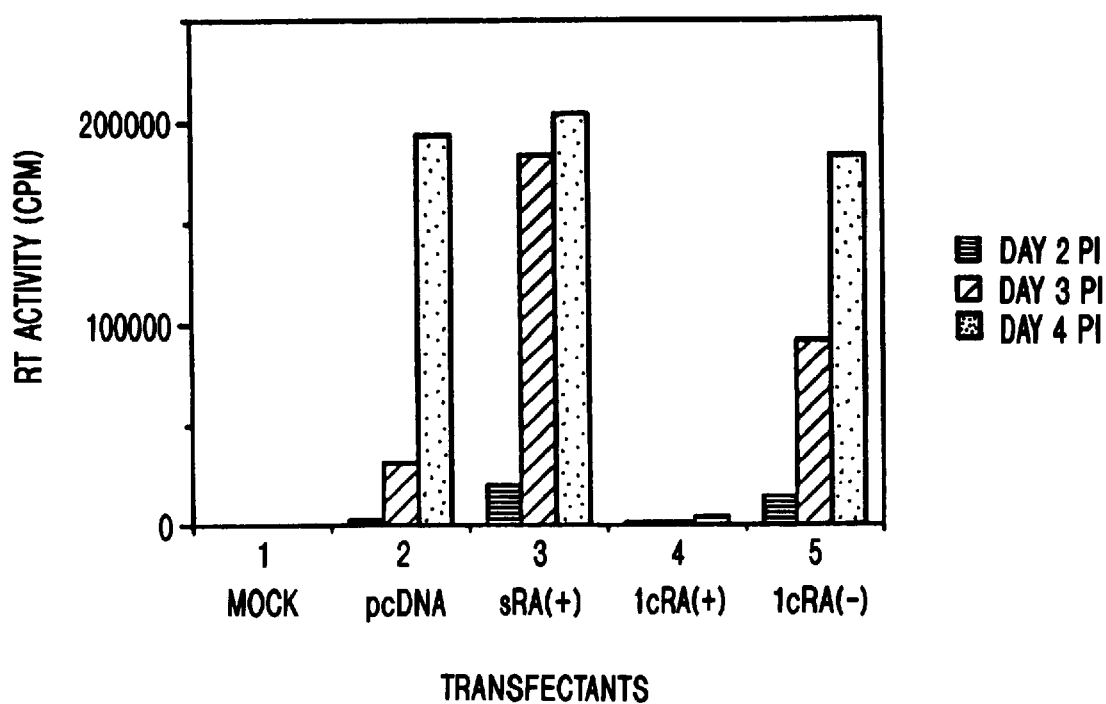
FIG. 2 shows reverse transcriptase assays of CEM cells transfected with the intracellular or secreted IL-1 receptor antagonist, and various controls.

Table 1 shows the effect of cellular COS cell lysates prepared from COS cells that were mock transfected, transfected with the vector, SRα, with or without the IL-1 receptor antagonist DNA sequence, or containing the sequence in the wrong orientation, or with a vector that encodes IL-2.

Table 2 shows the effect of COS cell lysates on IL-2 production from LBRM-33 cells when the lysates are prepared from mock transfected cells, cells containing the vector, SRα, that lacks the IL-1 receptor antagonist DNA sequence, the SRα vector that contains the IL-1 receptor antagonist DNA sequence, but in the wrong orientation, and the SRα vector that contains the IL-1 DNA sequence in the proper orientation.

Table 3 shows the effect of COS cell lysates on the inhibition of prostaglandin production in IL-1 inducible fibroblasts. COS cell lysates were prepared from COS cells that were mock transfected, transfected with the vector, SRα, with or without the IL-1 receptor antagonist DNA sequence, or containing the sequence in the wrong orientation.

DETAILED DESCRIPTION OF THE INVENTION

The invention described herein draws on previously published work. By way of example, such work consists of scientific papers, patents or pending patent applications. All of these publications and applications, cited previously or below, are hereby incorporated by reference.

The instant invention is composed of several unique methods and compositions. Each aspect of the invention will now be discussed separately.

"IL-1 Receptor Antagonist" refers to virtually any molecule that interferes with, or prevents the binding of IL-1 to its receptor. By way of example, and not by way of limitation, such antagonist are exemplified herein by two protein molecules that have been purified and cloned, that have interleukin-1 receptor antagonist activity have been reported. Hannum, et al., 1990, Nature, 343:336; Eisenberg, S., et al., 1990, Nature, 343:341; and Haskill, S., et al., U.S. Ser. No. 517,276, filed May 1, 1990. Other IL-1 Receptor Antagonist would include antibody that binds to, and interferes with or prevents the binding of IL-1 to its receptor. By antibody is intended any molecule that would have an anti-IL-1 receptor antibody combining site and would include, of course, polyclonal or monoclonal antibody or fragments derived therefrom, and molecules that have antibody binding activity made by recombinant methods. Monoclonal antibody to the IL-1 receptor may be produced using the general procedures described by Kohler, G. and Milstein, C., 1975, Nature, 256:495, which have been modified over the years as is known in the art. Antibody that binds to the receptor and interferes with IL-1 binding are readily identified using competition binding assays known in the art.

It is important to note that the definition of IL-1 receptor antagonist is not meant to exclude such molecules from having other properties. For example, it has been surprisingly discovered that in some instances such molecules have agonist activity as well. This is shown by the results in Example 6, wherein the intracellular IL-1 receptor antagonist down regulates CD4 expression on a T-cell line despite such cells not expressing detectable levels of IL-1.

"Cells" or "recombinant host" or "host cells" are often used interchangeably as will be clear from the context. These terms include the immediate subject cell, and, of course, the progeny thereof. It is understood that not all progeny are exactly identical to the parental cell, due to chance mutations or differences in environment As used herein the term "transformed" in describing host cell cultures denotes a cell that has been genetically engineered to produce a heterologous protein that possesses the activity of the native protein. Examples of transformed cells are described in the examples of this application. Bacteria are preferred microorganisms for producing the protein. Synthetic protein may also be made by suitably transformed yeast and mammalian host cells.

"Control sequences" refers to DNA sequences necessary for the expression of an operably linked coding sequence in a particular host organism. The control sequences which are suitable for procaryotes, for example, include a promoter, optionally an operator sequence, a ribosome binding site, and possibly, other as yet poorly understood, sequences. Eucaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

As used herein, the term "pharmaceutically acceptable" refers to a carrier medium which does not interfere with the effectiveness of the biological activity of the active ingredients and which is not toxic to the hosts to which it is administered. The administration(s) may take place by any suitable technique, including subcutaneous and parenteral administration, preferably parenteral. Examples of parenteral administration include intravenous, intraarterial, intramuscular, and intraperitoneal, with intravenous being preferred.

As used herein, the term "prophylactic or therapeutic" treatment refers to administration to the host of the cytokine inhibitor either before or after infection or cancer detection. If the cytokine inhibitor is administered prior to exposure to the infecting agent, the treatment is prophylactic (i.e., it protects the host against infection), whereas if administered after infection or initiation of cancer, the treatment is therapeutic (i.e., it combats the existing infection or cancer).

I. IL-1 Receptor Antagonists
A. Isolated/Cloned Protein Antagonist

FIG. 1 shows the amino acid sequence of the intracellular form of the IL-1 receptor antagonist (SEQ ID NO: 2). The cDNA sequence that encodes the molecule has been described in U.S. Pat. No. 517,276, filed May 1, 1990, and in Haskill, S. et al., *PNAS*, in press. The cDNA sequence (SEQ ID NO: 1) is on deposit with the American Type Culture Collection and the Cetus Microbial Culture Collection and has ATCC Accession No. 68449 and CMCC No. 3827. A secreted form of the intracellular IL-1 receptor antagonist is described by Hannum, et al., 1990, *Nature*, 343:336; Eisenberg, S., et al., 1990, *Nature*, 343:341. Carter et al., supra.

The IL-1 receptor antagonist cDNA sequence (SEQ ID NO: 1) can be expressed in a number of expression systems, and in a wide variety of cell types. Procaryotes most frequently are represented by various strains of *E. coli*. However, other microbial strains may also be used, such as bacilli, for example, *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., 1977, *Gene* 2:95. pBR322 contains genes for ampicillin and tetracycline resistance, and thus provides additional markers which can be either retained or destroyed in constructing the desired vector. Commonly used procaryotic control sequences, which are defined herein to include promoters for transcription initiation, optionally with an operator, along with ribosome binding site sequences, include such commonly used promoters as the beta-lactamase (penicillinase) and lactose (lac) promoter systems (Chang et al., 1977, *Nature* 198:1056), the tryptophan (trp) promoter system (Goeddel et al., 1980, *Nucleic Acids Res.* 8:4057) and the lambda derived $P_L$ promoter (Shimatake et al., 1981, *Nature* 292:128), and N-gene ribosome binding site, which has been made useful as a portable control cassette, U.S. Pat. No. 4,711,845, issued Dec. 8, 1987, and incorporated herein by reference in its entirety, which comprises a first DNA sequence that is the $P_L$ promoter operably linked to a second DNA sequence corresponding to the $N_{RBS}$ upstream of a third DNA sequence having at least one restriction site that permits cleavage within 6 bp 3' of the $N_{RBS}$ sequence. U.S. Pat. No. 4,666,848, issued May 19, 1987, and incorporated herein by reference in its entirety discloses additional vectors with enhanced expression capabilities. Also useful is the phosphatase A (phoA) system described by Chang et al., in European Patent Publication No. 196,864, published Oct. 8, 1986, incorporated herein by reference. However, any available promoter system compatible with procaryotes can be used.

In addition to bacteria, eucaryotic microbes, such as yeast, may also be used as hosts. Laboratory strains of *Saccharomyces cerevisiae*, Baker's yeast, are most used, although a number of other strains are commonly available. While vectors employing the 2 micron origin of replication are illustrated (Broach, 1983, *Meth. Enz.*, 101:307; U.S. Pat. No. 4,803,164, incorporated herein by reference in its entirety), other plasmid vectors suitable for yeast expression are known (see, for example, Stinchcomb et al., 1979, *Nature* 282:39, Tschempe et al., 1980, *Gene* 10:157 and Clarke et al., 1983, *Meth. Enz.* 101:300). Control sequences for yeast vectors include promoters for the synthesis of glycolytic enzymes (Hess et al., 1968, *J. Adv. Enzyme. Req.* 7:149; Holland et al., 1978, *Biochemistry* 17:4900).

Additional promoters useful in yeast host microorganisms and known in the art include the promoter for 3-phosphoglycerate kinase (Hitzeman et al., 1980, *J. Biol. Chem.* 255: 2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization (Holland, supra).

It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland et al., 1981, *J. Biol. Chem.* 256:1385) or the LEU2 gene obtained form YEp13 (Broach et al., 1978, *Gene* 8:121); however, any vector containing a yeast compatible promoter, origin of replication and other control sequences is suitable.

It is also, of course, possible to express genes encoding proteins in eucaryotic host cell cultures derived from multicellular organisms. See, for example, *Tissue Culture* Academic Press, Cruz and Patterson, editors (1973). Useful host cell lines include murine myelomas N51, VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., 1978, *Nature*, 273:113) viral promoters such as those derived from polyoma, Adenovirus 2, bovine papilloma virus, or avian sarcoma viruses, or immunoglobulin promoters and heat shock promoters. A system for expressing DNA in mammalian systems using the BPV as a vector is disclosed in U.S. Pat. No. 4,419,446, incorporated herein by reference in its entirety. A modification of this system is described in U.S. Pat. No. 4,601,978, incorporated herein by reference in its entirety. General aspects of mammalian cell host system transformations have been described by Axel in U.S. Pat. No. 4,399,216, issued Aug. 16, 1983. Also useful is gene amplification in eucaryotic cells as described by Ringold in U.S. Pat. No. 4,656,134, issued Apr. 7, 1987, incorporated herein by reference in its entirety. It now appears also that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes.

Plant cells are also now available as hosts, and control sequence compatible with plant cells such as the nopaline synthase promoter and polyadenylation signal sequences (Depicker et al., 1982, *J. Mol. Appl. Gen.,* 1:561) are available. Additionally, methods and vectors for transformation of plant cells have been disclosed in PCT Publication No. WO 85/04899, published Nov. 7, 1985, and incorporated herein by reference in its entirety.

It will be appreciated by those skilled in the art that although the precise chemical structure of the IL-1 receptor antagonist is shown in FIG. 1, and conservative amino acid changes or deletions or in the case of antibody antagonists are readily determined using known sequencing methods, the primary amino acid sequence of the protein may be augmented by derivatization using sugar moieties (glycosylation) or by other supplementary molecules such as lipids, phosphate, acetyl groups and the like, as well as by conjugation with saccharides, polyethylene glycols (PEGs) and polyoxyethylene glycols (POGs). Such modifications are included in the definition of peptide herein so long as the activity of the peptide, as defined above, is not destroyed. It is expected, of course, that such modifications may quantitatively or qualitatively affect the activity, either by enhancing or diminishing the activity of the protein in the various assays.

B. Antibody IL-1 Receptor Antagonists

Procedures for producing antibody, polyclonal or monoclonal, are well known in the art and may be adapted to produce IL-1 receptor antibody that binds to the receptor and prevents or interferes with IL-1 binding. The methods for generating monoclonal antibody are described by Kohler, G. and Milstein, C., 1975, *Nature,* 256:495. These initial studies involved fusing murine lymphocytes and drug selectable plasmacytomas to produce hybridomas. Subsequently, the technique has been applied to produce hybrid cell lines that secrete human monoclonal antibodies. The latter procedures are generally described in Abrams, P., 1986, *Methods in Enzymology,* 121:107, but other modifications are known to those skilled in the art. Regardless of whether murine or human antibody is produced, the antibody secreting cells are combined with the fusion partner and the cells fused with a suitable fusing agent, preferably polyethylene glycol, and more preferably polyethylene glycol 1000. The latter is added to a cell pellet containing the antibody secreting cells and the fusion partner in small amounts over a short period of time accompanied with gentle agitation. After the addition of the fusing agent, the cell mixture is washed to remove the fusing agent and any cellular debris, and the cell mixture consisting of fused and unfused cells seeded into appropriate cell culture chambers containing selective growth media After a period of several weeks, hybrid cells are apparent, and may be identified as to antibody production and subcloned to ensure the availability of a stable hybrid cell line.

The preferred antibody is human monoclonal antibody which can be prepared from lymphocytes sensitized with IL-1 receptor, or with cells that bear the same, either in vivo or in vitro by immortalization of antibody-producing hybrid cell lines, thereby making available a permanent source of the desired antibody. In vivo immunization techniques are well known in the art, while in vitro techniques are generally described by Luben, R. and Mohler, M., 1980, *Molecular Immunology,* 17:635, Reading, C. *Methods in Enzymology,* 121 (Part One):18, or Voss, B., 1986, *Methods in Enzymology,* 121:27. A number of in vitro immunization systems have been shown to be effective for sensitizing human B-cells. Reading, C., 1982, *J. of Immun. Methods,* 53:261.

Sensitized lymphocytes can be immortalized by viral transformation. The preferred viral transformation technique for human lymphocytes involves the use of Epstein-barr virus. The virus is capable of transforming human B-cells, and has been used to generate human monoclonal antibodies. Crawford, D. et al., 1983, *J. of General Virology,* 64:697; Kozbor, V. and Roder, J., 1983, *J. Immun. Today,* 4:72.

Another procedure whereby sensitized lymphocytes may be immortalized consist of a combination of the above two techniques, that is viral transformation and cell fusion. The preferred combination consist of transforming antibody secreting cells with Epstein-barr virus, and subsequently fusing the transformed cells to a suitable fusion partner. The fusion partner may be a mouse myeloma cell line, a heteromyeloma line, or a human myeloma line, or other immortalized cell line. PCT patent application Ser. No. 81/00957; Schlom et al., 1980, *PNAS (USA),* 77:6841; Croce et al., 1980, *Nature,* 288:488. The preferred fusion partner is a mouse-human hetero-hybrid, and more preferred is the cell line designated F3B6. This cell line is on deposit with the American Type Culture Collection, Accession No. HB8785. It was deposited Apr. 18, 1985. The procedures for generating F3B6 are described in European Patent Application, Publication No. 174,204.

Techniques applicable to the use of Epstein-Barr virus transformation and the production of immortal antibody secreting cell lines are presented by Roder, J. et al., 1986, *Methods in Enzymology,* 121:140. Basically, the procedure consist of isolating Epstein-Barr virus from a suitable source, generally an infected cell line, and exposing the target antibody secreting cells to supernatants containing the virus. The cells are washed, and cultured in an appropriate cell culture medium. Subsequently, virally transformed cells present in the cell culture can be identified by the presence of the Epstein-Barr viral nuclear antigen, and transformed antibody secreting cells can be identified using standard methods known in the art.

The hybridoma cells may be grown in appropriate cell culture media, and the supernatant screened for the presence of monoclonal antibody that prevents or interferes with binding of IL-1 to its receptor using, for example, an enzyme linked immunosorbent assay (ELISA). The latter is described by Engvall, E., 1977, *Med. Biol.,* 55:193. Basically, the procedure consist of coating flat-bottom 96 well microtitre plates with the appropriate source of IL-1 receptor antigen, preferably either purified IL-1 receptor or cells that carry the receptor, reacting the antigen with cell culture supernatant, removing the supernatant and then revealing the presence of antibody using a suitable second antibody that has been labelled with a reporter group. It is well known in the art that the reporter group is preferably a radioactive tracer or a fluorescent molecule. Procedures for isolating IL-1 receptor are described in European patent application, Publication No. 318,296, to Dower, S. K. et al., published May 31, 1989.

Those hybridomas that initially give a positive signal and therefore secrete antibody that bindings to the receptor are retested in the presence of IL-1 to determine if the antibody has IL-1 receptor antagonist activity. This assay is preferably conducted using labelled IL-1 and measuring a reduction in IL-1 binding to the receptor in the presence of antibody.

It will be apparent to those skilled in the art that while the preferred embodiment of the instant invention is anti-IL-1 receptor monoclonal antibody, singly or in combination, that the antibody(s) may be altered and still maintain biological activity. Thus, encompassed within the scope of the invention is antibody modified by reduction to various size fragments, such as F(ab')$_2$, Fab, Fv, or the like. Also, the hybrid cell lines that produce the antibody may be considered to be a source of the DNA that encodes the desired antibody, which may be isolated and transferred to cells by known genetic techniques to produce genetically engineered antibody. An example of the latter would be the production of single chain antibody having the antibody combining site of the hybridomas described herein. Single chain antibody is described in U.S. Pat. No. 4,704,692, or in U.S. Pat. No. 4,946,778. A second example of genetically engineered antibody is recombinant, or chimeric antibody. Methods for producing recombinant antibody are shown in U.S. Pat. No. 4,816,567, inventor Cabilly, et al.; Japanese patent application, Serial No. 84169370, filed Aug. 15, 1984; U.S. patent application, Ser. No. 644,473, filed Aug. 27, 1984; British patent application 8422238, filed on Sep. 3, 1984; Japanese patent application, No. 85239543, filed Oct. 28, 1985; U.S. patent application, Ser. No. 793,980 on Nov. 1, 1985; U.S. patent application, Ser. No. 77,528, filed Jul. 24, 1987. Also, British patent application, No. 867679, filed Mar. 27, 1986 describes methods for producing an altered antibody in which at least parts of the complementary determining regions (CDRs) in the light or heavy chain variable domains have been replaced by analogous parts of CDRs from an antibody of different specificity. Using the procedures described therein it is feasible to construct recombinant antibody having the CDR region of one species grafted onto antibody from a second species that has its CDR region replaced. The preferred embodiment in this instance is a murine anti-IL-1 receptor antibody CDR region that replaces the CDR region of human antibody. Hybrid cells produced by fusing antibody secreting cells and an appropriate fusion partner, or Epstein-Barr virus transformed cells that produce the desired antibody can be identified using convenient immunochemical screening techniques.

Regardless of whether the antibody being screened is monoclonal, recombinant, single chain etc., the assay described above may be employed to identify IL-1 receptor antagonists.

C. Formulation of IL-1 Receptor Antagonists

It will be appreciated by those skilled in the art that the IL-1 receptor antagonists described herein can be administered to mammals, including humans, either alone or in combination with other anti-inflammatory agents, or they may be combined with various pharmaceutically acceptable diluents or carriers. Such are widely known to those skilled in the art and are formulated according to standard pharmaceutical practices.

Exemplary diluents include physiologic saline, or buffered saline, as well as Ringer's and dextrose injection fluid, and dextrose saline and lactated Ringer's injection or diluent solutions containing additional therapeutic agents, preferably antibiotics or antibodies known to be efficacious in the treatment of inflammatory conditions.

II. Leukocyte Preparation/Labelling

Leukocyte adherence can be measured using several assays known in the art, and the preferred assay is described by Charo, et al., 1985, *Blood*, 65:473. Briefly, the assay consists of labelling leukocytes with an appropriate label, incubating the leukocytes with endothelial cells and determining the number of leukocytes that adhere. Preferably the cells are labelled with a gamma ray emitting isotope and the preferred labels are $^{111}$Indium-oxide or $^{51}$chromium.

Leukocytes may be isolated from human donors using standard techniques. This generally consists of isolating blood in a physiologically balanced salt solution containing an appropriate anticoagulant, and separating the leukocytes by an appropriate separation step, preferably on Ficoll-Hypaque gradients. Contaminating erythrocytes can be removed by hypotonic lysis. The resulting leukocytes are suspended in a physiologically buffered solution, pH 7.4. The preferred physiological buffered solution is Hank's balanced salt solution that is calcium and magnesium free.

The isolated leukocytes can then be labelled by incubating them for an appropriate time, generally 15 minutes, with the desired radioisotope at a predetermined concentration. The radiolabelled cells are washed to remove unincorporated label, and then suspended in an appropriate solution to perform the adhesion assay described below.

III. Endothelial Cell Preparation/Culture

Endothelial cells can be prepared from a number of sources and by several techniques known in the art. Preferably they are obtained from human umbilical veins using the procedure of Charo et al., above. Generally, endothelial cells are isolated by enzymatic digestion of the umbilical veins using, preferably, collagenase as described by Jaffe, E. A., et al., 1973, *J. of Clin. Invest*, 52:2745. The cells are grown on an appropriate tissue culture substratum, preferably gelatine-coated surfaces.

The endothelial cells may be grown in a variety of tissue culture media containing appropriate supplements such as an appropriate concentration of fetal calf serum, and other supplements/additives routinely utilized by those skilled in this art that are recognized as being favorable for endothelial cells. The endothelial cells may be passaged with a dilute solution of an appropriate protease, and if desired a metal ion chelator. Preferably a solution consisting of 0.05 to 0.25% trypsin and 0.02% EDTA is used. To ensure that the cells are indeed endothelial cells, they are tested by immunofluorescence for Factor VIII antigen, a known endothelial cell marker.

IV. Leukocyte/Endothelial Cell Adhesion Assay

Leukocyte adherence to endothelial cell monolayers may be determined as follows. Early passage endothelial cells, generally not beyond the fifth passage, are cultured on an appropriate substratum and in a suitable cell culture medium. The culture substratum is preferably pre-coated with an appropriate substance that enhances the adherence of the endothelial cells. Several such substances are known including fibronectin, poly-L-lysine, gelatin and laminin. Fibronectin is preferred. An appropriate culture substratum is a 96-well micro titer plate, and a suitable medium is Medium 199 containing fetal calf serum and other supplements known to be beneficial for the growth and maintenance of endothelial cells that are well known to those skilled in the art. The endothelial cell monolayer is washed with a physiologically balanced salt solution containing a reduced amount of fetal calf serum, preferably 1%. The preferred solution is RPMI supplemented with 1% fetal calf serum. Prior to the adhesion step, endothelial cells and/or leukocytes are incubated with IL-1 to induce membrane adhesion molecules. Preferably 10 U/ml IL-1β is added to the endothelial cells for 4 hours.

The endothelial cell monolayer containing added leukocytes preferably $^{111}$Indium monocytes are incubated for a time sufficient to permit maximum adherence of the leukocytes, and preferably this is conducted at 37° C. for 30 minutes in an appropriate cell culture atmosphere. Generally this would consist of incubating the cells for the assay period in 5% $CO_2$, 95% air, and 95% humidity. Next, non-adherent leukocytes are removed by any number of techniques known in the art, and the number of leukocytes adherent to the endothelial cell monolayers determined by measuring the amount of radioisotope associated with the endothelial cell monolayer. Controls are run that take into account basal binding, i.e., binding to endothelial cells not activated with IL-1.

In a typical experiment run in quadruplicate, the assay is highly reliable, giving standard deviations less than 10%, and usually less than 5%, of mean values. Typically the results are expressed as the percent of leukocytes added to the endothelial cells that remain adherent after non-adherent cells have been removed.

Using the above assay, typically the IL-1 receptor antagonist is added over a range of concentrations and preferably at $10^{-4}$ M. This volume is then suitably diluted in an appropriate medium, preferably RPMI containing 1% fetal calf serum to give the desired final concentration to be tested.

The endothelial cells were activated with 10 U/ml of IL-1β (Genzyme Corp.) for at least 4 hours in RPMI with 1% fetal calf serum prior to the addition of the leukocytes. IL-1 causes the induction of ICAM expression on endothelial surfaces which is a receptor for leukocyte integrin binding.

V. Determination of the Effectiveness of an IL-1 Receptor Antagonist in Graft Versus Host Disease Using Primary Mixed Lymphocyte and Phytohemagglutinin Assays The mixed lymphocyte response (MLR) and phytohemagglutinin A (PHA) assays are valuable for identifying immune suppressive molecules in vitro that are useful for treating graft versus host disease. The results obtained from these assays are generally predictive of their in vivo effectiveness.

The in vitro mixed lymphocyte assay is presently employed in the clinical setting as an indicator of histocompatibility, and is premised on the transformation of resting genetically dissimilar lymphocytes into cells which synthesize DNA and undergo proliferation. It has been demonstrated that incompatibility at the major histocompatibility complex is mainly responsible for this phenomenon.

A second assay widely used to study immune responsiveness is mitogenic stimulation of lymphocytes with mitogenic substances of plant origin. The most widely used plant molecule is PHA. Although PHA stimulates DNA synthesis non-specifically in a large number of lymphocytes, unlike true antigenic stimulation which causes mitogenesis of subpopulations of lymphocytes, the susceptibility of a patient's lymphocytes to PHA stimulation has been shown to correlate with the overall immune responsiveness of the patient.

Thus, it will be appreciated as to both the mixed lymphocyte and PHA assay that they are valuable for identifying immune suppressive molecules in vitro, and that the results obtained therefrom are generally predictive of their in vivo effectiveness.

In addition to the above immunosuppressive assays, a secondary mixed lymphocyte reaction assay may also be used. The secondary mixed lymphocyte assays differs from the primary mixed lymphocyte reaction assays in that they employ many more primed responder cells that are responsive to the primary stimulating cells. The presence of such responsive cells is a reflection of immunological memory in an ongoing immunological response. The protocol for carrying out a secondary mixed lymphocyte assay involves performing a primary lymphocyte assay as described above, and recovering viable cells about 9–10 days after the primary mixed lymphocyte reaction exhibits little or no cell proliferation. Generally between 10% to 50% of the original input cells are recovered in viable condition. These cells are then used in the secondary mixed lymphocyte reaction.

The procedure for carrying out a secondary mixed lymphocyte reaction is described by T. Meoen, *Immunological Methods,* Eds I. Lefkoivits and B. Pernis, Economic Press, New York (1979). It will be appreciated that described therein is a method for carrying out secondary lymphocyte reactions using mouse cells, however such methods are generally applicable to performing secondary mixed lymphocyte reactions using human cells with modifications that are well known to those skilled in the art.

Using one or all of the above assays, the immune suppressive effectiveness of IL-1 receptor antagonists can be determined, and thus their use in treating graft versus host disease defined. The assays can be performed as is known in the art, and with or without added IL-1 receptor antagonists. The antagonists would be added to the assay reaction mixture at various concentrations to ascertain the concentration that is optimally effective.

Having described what the applicants believe their invention to be, the following examples are presented to illustrate the invention, and are not to be construed as limiting the scope of the invention. For example, variation in the source, type, or method of producing antibodies; different labels and/or signals; test supports of different materials and configurations; different immobilization methods may be employed without departing from the scope of the present invention.

EXAMPLE 1

Affect of IL-1 Receptor Antagonist on Monocyte Adhesion to Endothelial Cell Monolayers COS cell lysates containing IL-1 receptor antagonist were tested for their capacity to interfere with, or block adhesion of monocyte to human endothelial cell monolayers. A variety of controls were also run including a buffer control or performing the assay using lysates prepared from cells transfected with the vector, SRα, without the IL-1 receptor antagonist DNA sequence (SEQ ID NO: 1) or with the sequence in the wrong orientation. Also, the effects of IFN, and IL-2 were tested. COS cells were cultured in MEM (minimal essential medium) with high glucose, +10% FBS.

COS cell lysates were prepared from COS-7 cells that were transfected with plasmid DNA containing the PstI fragment, which contains all of the 5' untranslated, the complete open reading frame, and 60 based pairs of the 3' untranslated region. Transfection was achieved using the DEAE-dextran/chloroquine technique as described by Wong, G. G. et al., 1985, *Science,* 228:810. Three days subsequent to the transfection, the supernatant and cells were freeze thawed to obtain a culture lysate. Suitable dilutions of the lysate were employed in the experiments described below.

The endothelial cells were isolated from human umbilical cords by mild collagenase digestion. Collagenase was obtained from Worthington Corporation, Freehole, N.J., and the general procedure is described by Jaffe, E. A., et al, 1973, *J. of Clin. Invest.,* 52:2745. The cells obtained from collagenase digestion were grown on gelatin-coated flasks in cell culture medium consisting of medium 199 (Gibco, Grand Island, N.Y.) buffered with 25 mM Hepes. The media was supplemented with 20% fetal calf serum. The media also contained 60 µg/ml sodium heparin (Sigma Corporation, St. Louis, Mo.), 2 mM L-glutamine and 50 µg/ml of bovine hypothalamus extract. The bovine tissue was obtained from Pel Freeze, Rogers, Ak. The hypothalamus extract serves as a source of endothelial cell growth factor. The pH of the cell culture media was 7.4.

After the endothelial cells reach confluency, they are passaged with 0.25% trypsin containing 0.02% EDTA, and subsequent subculturing was performed using the same solution. The cells were exposed to this mixture in Hank's balanced salt solution at room temperature for about 1 minute.

Finally, approximately $2\times10^4$ cells/well were seeded in microtiter plates. The endothelial cell nature of the cells was confirmed both by their cobblestone morphology at confluency, and the fact that they stained positive for Factor VIII antigen by indirect immunofluorescence. The latter procedure is well known in the art, and is described by Jaffe, E. A., 1973, *J. Clin. Invest.*, 52:2745.

Monolayers of endothelial cells, prior to the fifth passage, were established on polystyrene, 96-well flat bottom micro titer plates (Coming Corporation) in Medium 199 containing 20% fetal calf serum 25 mM hepes, pH 7.4, and the other supplements described above. The surfaces of the micro titer plates were incubated with 6.4 μg/ml human plasma fibronectin for 30 minutes at 25° C. prior to plating the endothelial cells. The solution of fibronectin was removed before addition of endothelial cells.

The endothelial cell cultures were used when they were confluent The endothelial cell monolayers were washed with RPMI plus 1% fetal calf serum and incubated with 10 U/ml of IL-1β to activate the endothelial cells, and 1:10 dilutions of COS cell lysates. Next, labelled monocytes at a final concentration of $5\times10^5$ cells per well were added and allowed to settle for 30 minutes onto the endothelial cell monolayers.

Human monocytes were obtained from venus blood from several healthy adult volunteers using an anti-coagulant (10% heparin) followed by centrifugation of the blood on Ficoll-Hypaque gradients. Contaminating erythrocytes were removed by hypotonic lysis. The remaining cell population consisted of 95 to 98% polymorphonuclear leukocytes, and these cells were suspended at a concentration of $50\times10^6$ cells per ml in Hank's balanced salt solution, pH 7.4.

The monocytes were labelled with $^{111}$Indium-oxide (100 μCi/$10^8$ PMNs) (10 mCi/mml, Amersham Corp.). Labelling occurred at room temperature in Hank's solution for 15 minutes, after which the labelled cells were isolated by centrifugation for 5 minutes, and to remove residual unincorporated label, washed twice with Hank's balanced salt solution, and then suspended in RPMI supplemented with 1% fetal calf serum.

As mentioned above, $5\times10^5$ of the labelled monocytes were added per well in 96-well micro titer plates. Incubations were conducted for 30 minutes at 37° C., in a tissue culture incubator in an atmosphere of 5% $CO_2$, 95% air.

After the 30 minute incubation period, during which the monocytes adhere to the endothelial cell monolayer, the micro titer plates were filled and sealed with adherent transparent plastic (Dynatech, Inc., Alexander, Va.), inverted and centrifuged using a micro plate carrier, obtainable from Beckman Instruments Corp. Centrifugation was at 75×g for 5 minutes at room temperature. This effectively removed nonadherent PMNs from the endothelial cell monolayers. Next, the plates were blotted dry and the number of monocytes that remained adherent to the endothelial cell monolayers was determined using a gamma counter. The results are shown in Table 2, and they are expressed as the percent of monocytes that remained adherent to the endothelial cell monolayers. The experiments were conducted using monocytes isolated from two individuals, donor 1 and donor 2.

TABLE 1

Inhibition of Binding of Human Peripheral Blood Monocytes to IL-1 Stimulated Endothelial Cells

| COS Lysate | Donor 1 | | Donor 2 | |
|---|---|---|---|---|
| | % Binding | % Change | % Binding | % Change |
| Mock | 14.9 | 7 | 17.3 | 5 |
| SRα | 14.1 | 0 | 14.4 | −15 |
| IL-2 | 14.8 | 6 | 17.2 | 4 |
| icIL-1ra (anti-sense) | 14.4 | 3 | 15.7 | −6 |
| icIL-1ra (sense) | 6.9 | −59 | 6.8 | −66 |

The data shown in Table 1 are instructive in several aspects. First, neither COS cell lysates prepared from mock transfected cells, nor lysates prepared from the SRα vector lacking the IL-1 receptor antagonist DNA coding sequence cause a significant or reproducible decrease in monocyte adhesion to the endothelial cell monolayer. Similarly, neither COS cell lysates prepared from cells transfected with IL-2 vector nor plasmid containing IL-1 receptor antagonist DNA in the anti-sense orientation effect the adhesion of monocytes. In contrast, however, lysates prepared from COS cells transfected with icIL-1ra sense DNA reduce the number of monocytes that adhere to the endothelial cell layer by greater than 50% from both donors.

These results convincingly establish that an IL-1 receptor antagonist can reduce the adhesion of monocytes to endothelial cells and thus have positive medical applications as presented in Examples 3 and 4, below.

EXAMPLE 2

Effect of IL-1 Receptor Antagonist on IL-1 Dependent IL-2 Production

To further determine the effectiveness of the IL-1 receptor antagonist to compete with IL-1 for binding to the IL-1 receptor, the capacity of the antagonist to inhibit IL-1 induced production of IL-2 from LBRM-33 1A5 cells was determined. LBRM-33 1A5 cells are known to produce IL-2 in response to IL-1. LBRM-33 is described by Gillis, S. et al., 1981, *PNAS*, 78:1133 and is on deposit with the ATCC with Accession No. CRL 8079. IL-2 levels were measured using a cellular assay involving a cell line that requires IL-2 for survival. The cell line employed was HT-2, and the levels of IL-2 were determined by $^3$H-thymidine incorporation after an 18–24 hour period. HT-2 cells are a mouse IL-2 dependent cell line which die in the absence of IL-2. The assay is described by Gillis et al., 1978, *J. of Immunol.*, 120:2027.

LBRM-33 cells were induced with 0.08 U/m IL-1β, obtained from Cistron Biotechnology, Pine Brook, N.J., plus 2.5 μg/ml PHA, obtained from Sigma Chemical Corporation, St. Louis, Mo., and various dilutions of the COS cell lysates. After 24 hours LBRM-33 cell culture supernatants were tested for IL-2 using the HT-2 cell assay as described by Gillis, et al., above.

TABLE 2

Inhibition of IL-1 Induced IL-2 Production by LBRM-33 Cells

|  |  | % Control HT-2 Proliferation | | | | |
|---|---|---|---|---|---|---|
| COS Lysate | Dilution: | 1:8 | 1:16 | 1:32 | 1:64 | 1:128 |
| Mock |  | 42 | 70 | 86 | 91 | 86 |
| SRα |  | 43 | 71 | 88 | 90 | 106 |
| IL-2 |  | 448 | 456 | 460 | 488 | 373 |
| icIL-1ra (anti-sense) |  | 38 | 62 | 86 | 85 | 90 |
| icIL-1ra (sense) |  | 6 | 21 | 46 | 57 | 69 |

It is apparent based on the results shown in Table 2 that lysates prepared from COS cells transfected with icIL-1ra sense DNA inhibit the production of IL-2 from LBRM-33 cells. In contrast, COS cell lysates prepared from mock transfected cells, or cells infected with the vector SRα that did not contain the intracellular IL-1 receptor antagonist DNA coding sequence show no inhibitory effect. Two additional lysate controls were run. COS cells transfected with SRα encoding IL-2 and lysates prepared from cells transfected with plasmid containing IL-1 receptor antagonist DNA in the anti-sense orientation. Neither control caused a significant inhibition of IL-2 production. Note that lysates prepared from COS cells transfected with SRα encoding IL-2 exhibit significant IL-2 levels in the assay. This is because IL-2 is carried over from the IL-2 transfection, and thus produces an apparent positive signal in the HF-2 assay.

The above results clearly establish that the intracellular form of the IL-1 receptor antagonist effectively blocks the IL-1 induced production of IL-2.

EXAMPLE 3

Inhibition of Prostaglandin Production

The effect of the intracellular IL-1 receptor antagonist on prostaglandin production by human fibroblasts was determined NHDF-194 human fibroblasts were obtained from Clonetics Corporation, San Diego, Calif., and cultured using standard methods. Prostaglandin, specifically prostaglandin $E_2$, was assayed by RIA using a commercial kit available from Dupont Corporation, NEK-020. The results are shown in Table 3.

COS cell lysates were prepared from COS cells that were transfected with the vector, SR-α, with the IL-1 receptor antagonist DNA sequence, or containing the sequence in the wrong orientation. Inhibitor and IL-1 were added to the appropriate lysate at a 150 U/ml ($10^6$ U/mg, Cistron Corporation) and incubated with $2 \times 10^4$ fibroblasts for 18 hours, after which cultures supernatants were collected and assayed for prostaglandin $E_2$. Table 3 shows that fibroblasts not exposed to IL-1 do not exhibit elevated levels of prostaglandin, whereas those that were exposed to IL-1 do produce prostaglandin in the range of about 1000 pg/well (0.2 ml). Inhibition of prostaglandin production was observed only with COS cell lysates prepared from COS cells transfected with the intracellular IL-1 receptor antagonist oriented in the correct orientation. The inhibited level observed is about an order of magnitude below either of the controls.

TABLE 3

IcIL-1ra* Blocks IL-1 Induced Fibroblast Prostaglandin Production

|  |  | PGE2 (pg) | |
|---|---|---|---|
| Sample |  | No IL-1 | 150 U/ml IL-1 |
| Control |  | 47–51 | 790–1072 |
| icIL-1ra* |  |  |  |
| Correct Orientation | 1:4 | 58 | 88 |
|  | 1:8 | 48 | 114 |
|  | 1:16 | 53 | 157 |
| Wrong Orientation | 1:4 | 89 | 1700 |
|  | 1:8 | 62 | 1120 |
|  | 1:16 | 50 | 990 |

*Intracellular IL-1 Receptor Antagonist

EXAMPLE 4

Prophylactic Use of the Intracellular IL-1 Receptor Antagonist For Reducing Ischemic Injury The intracellular IL-1 receptor antagonist can be used to reduce or prevent ischemic injury as exemplified by the following example. An experimental system with which to test the effectiveness of the intracellular IL-1 receptor antagonist is a rat ligation model. Briefly, this would consist of using rats that weight about 300 grams, anesthetizing them with a suitable anesthetic such as pentabarbial and performing a thoracectomy. Next, the left anterior descending coronary artery would be ligated at its origin, and the ligation maintained for about 1 hour. This effectively reduces or eliminates blood flow thus setting the stage for ischemic injury to the artery. Subsequently, the ligation would be released to allow reperfusion, and the reperfusion permitted to take place for 30 minutes to 1 hour. For the experimental group of animals, reperfusion would be accompanied by administering into the femoral vein appropriate amounts of the intracellular IL-1 receptor antagonist, and this would range from 50 μg/–1000 μg/per kilogram of body weight. The control group would receive a saline solution lacking the receptor antagonist.

Twenty-four hours following reperfusion, the rats would be reanesthetized, the heart removed, and the left ventricles cut parallel to the atrioventricular space sulcus into slices. The tissue slices may be stained at 37° C. for 15 minutes using an appropriate dye, particularly triphenyltetrazolium chloride, and the size of the infarction determined by weighing the tissue.

It would be expected that the size of infarcts in tissue taken from rats that receive the intracellular IL-1 receptor antagonist would be decreased by about 50% compared to tissue removed from control animals.

EXAMPLE 5

IL-1 Receptor Antagonist as a Cancer Therapeutic

IL-1 is an autocrine growth factor for certain cancers. Tsai and Gaffney, 1987, *JNCI*, 79:77–81. Thus, the IL-1 receptor antagonist inhibitor would interfere with the autocrine activity of IL-1 and be an effective chemotherapeutic for the treatment of this form of cancer. The inhibitor can be administered in an effective amount, with the dosage of the inhibitor normally being determined by the prescribing physician. It is to be expected that the dosage will vary according to the tumor type, tumor mass, as well as the age, weight, and response of the individual patient. Typically, the amount of inhibitor administered per dose will be in the range of about 0.1 to 25 mg/kg of body weight, with the preferred dose being about 0.1 to 10 mg/kg of patient body weight. For parenteral administration, the inhibitor will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the inhibitor. The preparation of such solutions is within the skill of the art. Typically, the IL-1 receptor antagonist inhibitor will be formulated in such vehicles at a concentration of about 1–8.0 mg/ml.

EXAMPLE 6

IL-1 Receptor Antagonist as an AIDS Medicament

Using the materials and methods described above or that are well known in the art, the IL-1 receptor antagonist cDNA (SEQ ID NO:1) presented in FIG. 1 was transfected into a human T-cell line, CEM, and shown to down regulate the expression of CD4 as revealed by FACS using anti-CD4 antibody. CEM cells transfected with the antagonist had no detectible CD4 on the cell surface, and such cells when exposed to HIV are not infected by virus as revealed by reverse transcriptase activity (FIG. 2). FIG. 2 also shows that the secreted form of the IL-1 receptor antagonist is not effective in blocking HIV infection, and FACS sorting revealed that this molecule does not down regulate CD4 expression.

It is apparent, based on the above results, that the intracellular form of the IL-1 receptor antagonist, or the secreted form without its leader sequence, would be useful to prevent or control HIV infection by removing CD4 positive T-cells from a patient, transfecting the cells with either antagonist, but preferably the intracellular form, and returning the cells to the patient. Such cells would no longer be subject to infection by the virus, and thus significantly extend the life span of the patient.

EXAMPLE 7

Intracellular IL-1 Receptor Antagonist for the Detection of Endometrial Cancer To determine whether alterations of IL-1 mediated events by receptor antagonists may further be implicated in the pathogenesis of cancer we studied the expression of IL-1 and IL-1 receptor antagonists in normal endometrium and endometrial cancers. RNA was extracted from 11 benign endometrium and 20 endometrial cancers. mRNA expression of IL-1, secreted (sIL-1ra), and intracellular (icIL-1ra) IL-1 receptor antagonist was determined using reverse transcriptase polymerase chain reaction. IL-1 was expressed by normal endometrium and endometrial cancer, expression did not differ between these two tissue types. sIL-1ra was not expressed by any endometrial sample. However, normal samples showed minimal expression of icIL-1ra while endometrial cancers showed significantly higher levels of expression, up to 100×(p=0.03). Because icIL-1ra transcripts were increased in endometrial cancers, tissue samples were stained with a polyclonal antibody recognizing IL-1 receptor antagonists. Normal endometrium showed epithelial staining and no stromal staining for IL-1ra In contrast, in endometrial cancers the stromal component stained strongly for IL-1ra We conclude that icIL-1ra mRNA expression is increased in endometrial cancers and corresponds to increased IL-1ra seen in stromal tissue in neoplasias.

The present invention has been described with reference to specific embodiments. However, this application is intended to cover those changes and substitutions which may be made by those skilled in the art without departing from the spirit and the scope of the appended claims.

Ovarian cancer cells expressing retrovirally transduced intracellular interleukin-1 receptor antagonists (icIL-1ra) respond in a fashion analogous to those that constitutively express icIL-1ra. While expression of icIL-1ra does not affect cell growth or block immediate signaling through the IL-1 receptor, it does attenuate IL-1-inducible gene expression. Following exposure to IL-1β, cells expressing icIL-1ra were found to have diminished mRNA kinetics for several IL-1-inducible genes including IL-8, GRO or A20/MAD-6. In response to continuous IL-1β exposure, icIL-1ra-positive cells were found to be incapable of maintaining GRO mRNA expression. This appears to be a consequence of post-transcriptional regulation. The results suggest that icIL-1ra is a unique intracellular inhibitor with the capacity to attenuate IL-1-inducible gene expression.

The ovarian cancer cell lines OC-194 and OC-494 were kindly provided by Dr. O. Martinez-Maza, UCLA, Los Angeles. Cell lines were maintained in monolayer cultures in DMEM/F12 medium supplemented with 10% fetal bovine serum (Hyclone, Ogden, Utah). The cervical cancer cell lines C33, HT-3, ME-180 and SiHa were obtained from and maintained according to directions from the American Type Culture Collection.

The cDNAs encoding human icIL-1ra and secreted interleukin-1 receptor antagonist (sIL-1ra), isolated from an adherence-induced monocyte cDNA library, were cloned into the plasmid pLXSN. Clonal amphotropic retroviral packaging cells producing icIL-1ra (LlC33) and sIL-1ra (SRAM3) were derived from PA317 cells with a retroviral vector titer of 1–3×10$^6$ colony-forming units (CFU)/ml.

Cells (approximately 5×10$^4$) were plated in 24-well plates and allowed to adhere overnight after which the medium was removed, cells were washed once in sterile PBS, and viral stock was added in 0.3–0.5 ml with 5 μg/ml polybrene for 3 hours. Following incubation, the virus-containing supernatants were removed and replaced with fresh complete culture medium. After 3 days, the cells were trypsinized, replated in 60 mm tissue culture dishes and drug selection was initiated with a G418 concentration of 200 μg/ml. G418 concentration was increased in 200 μg/ml increments on a weekly basis for 4 weeks to a final concentration of 800 μg/ml, by which time all uninfected cells were dead.

For Western analysis, cells were plated in 60 mm dishes at a concentration of approximately 1×10$^5$. Following an overnight incubation, cells were lysed directly in the dish by scraping into 200 μl of 2× Laemmli sample buffer. The samples were harvested, immediately boiled for 3 minutes, and frozen at −20° C. until analyzed. For detection of IL-1ra, proteins were separated on 12% SDS-PAGE, transferred to nitrocellulose membranes by standard protocols, and blocked for 1 h in 5% powdered non-fat milk in PBS (milk buffer). The primary anti-IL-1ra antibody (icra-KLH, Chiron Corp., Emeryville, Calif.) 1:1000 dilution in milk buffer, was incubated overnight, rotating at room temperature. Membranes were washed 3 times in PBS prior to the addition of a secondary antibody (alkaline phosphataseconjugated goat anti-rabbit, Sigma) at a 1:1000 dilution in milk buffer for 1 hour at room temperature. Membranes were washed 3 times in PBS prior to development with Western Blue substrate (Promega, Madison, Wis.). For detection of IκBα, the protocol was identical except that cells were treated with recombinant IL-1β (Intergen, Purchase, N.Y.) 1 ng/ml for 20 minutes, proteins separated on 10%. SDS-PAGE, and the primary antibody #9 (Chiron) used at a 1:300 dilution.

For Northern analysis, total RNA was isolated from ovarian cancer cells using the guanidinium isothiocyanate/cesium chloride ultracentrifugation protocol. Purified RNA (3–5 μg/lane) was electrophoresed through 1% agarose/formaldehyde gels and immobilized on Nytran® nylon membrane (Schliecher and Scheull, Keene, N.H.) by capillary action. Blots were pre-hybridized in 6× SSPE, 0.5% SDS, 5× Denhardt's solution, 200 μg/ml ssDNA, 50% formamide, at 42° C. for at least 2 hours prior to the addition of the probe. cDNA probes for A20/MAD-6, GRO, and IL-8 were radiolabeled with $^{32}$P-dCTP by random priming. Blots were sequentially washed in 2× SSPE with 0.1% SDS for 30 min at room temperature at 42° C. and once in 0.2× SSPE with 0.1% SDS for 30 minutes at 56° C. Blots were exposed to autoradiography film (Kodak XAR-5) with intensifying screens at −70° C. for 1–9 days. Densitometry was performed on the autoradiographs using the NIH Image 1.07 Macintosh Software.

Nuclear isolations and run-on transcriptions were performed using slight modifications of established procedures. Following culture, cell monolayers (1.5×10$^7$ cells/treatment group) were washed twice with ice-cold PBS, gently scraped into PBS with a rubber policeman, collected into polypropylene tubes, and pelleted by centrifugation at 500×g. The resulting cell pellets were each suspended in 1.5 ml of ice-cold NP-40 lysis buffer A (10 mM Tris-HCl, pH 7.4, 10 mM NaCl, 3 mM MgCl$_2$, 0.30% w/v Nonidet P-40, and 100 U/ml RNasin). Cell lysis was allowed to proceed for 10 minutes on ice. Nuclei were then collected by centrifugation at 500×g for 5 minutes and subsequently washed twice with 1 ml of NP-40 lysis buffer B (10 mM Tris-HCl, pH 7.4, 10 mM NaCl, 3 mM MgCl$_2$, 0.3% w/v Nonidet P-40, and 30 U/ml RNasin). Run-on transcriptions were initiated by suspending the washed nuclei in 100 μl of reaction mix (10 mM Tris-HCl, pH 8.0, 5 mM MgCl$_2$, 100 mM KCl, 1 mM dithiothreitol, 40 U/ml RNasin, 500 mM each of GTP, CTP and ATP, and 100 mCi of α-$^{32}$P-UTP (3000 Ci/mmol)) and incubating the suspension at 30° C. for 30 minutes, mixing every five minutes. Reactions were terminated by the addition of 500 μl of a solution containing 4M guanidinium isothiocyanate, 25 mM sodium citrate, 100 mM 2-mercaptoethanol, and 0.5% w/v sarkosyl. The $^{32}$P-labeled run-on RNA was subsequently purified by phenol/CHCl$_3$ extraction, precipitated with 2-propanol, and denatured for 30 minutes at 60° C. in a solution consisting of 6× SSPE, 1× Denhardt's, 0.5% w/v sodium dodecyl sulfate, and 50% v/v formamide. Total cpms were equilibrated for all sample points prior to hybridization to Nytran filters of slot-blotted cDNAs (2.5 μg each) for β-actin, IL-8, GRO, A20/MAD-6, and c-jun. As negative hybridization controls, the empty cloning vectors pEMSV (pEMSVscribea2; Hal Weintraub, Fred Hutchinson Cancer Research Center, Seattle, Wash.) and pBS+ (Stratagene, La Jolla, Calif.) were also included on the filters. Hybridizations were carried out at 42° C. for 60 hours in a solution consisting of 6× SSPE, 1× Denhardt's, 0.5% sodium dodecyl sulfate, 50 μg/ml denatured salmon sperm DNA, and 50% v/v formamide. Following hybridization, the filters were washed twice for 30 min in 2× SSPE, 0.1% SDS at 42° C., twice for 30 min in 0.2× SSPE, 0.1% SDS at 42° C., and once for 20 min in 0.2× SSPE, 0.1% SDS at 65° C. before exposure to Kodak XAR film. Subsequent to autoradiography, the filters were exposed to a phosphorimager screen for quantitation of run-on activity (Molecular Dynamics ImageQuant 3.3).

EXAMPLE 8

Expression of icIL-1ra in ovarian and cervical cancer cell lines

Figure 3:
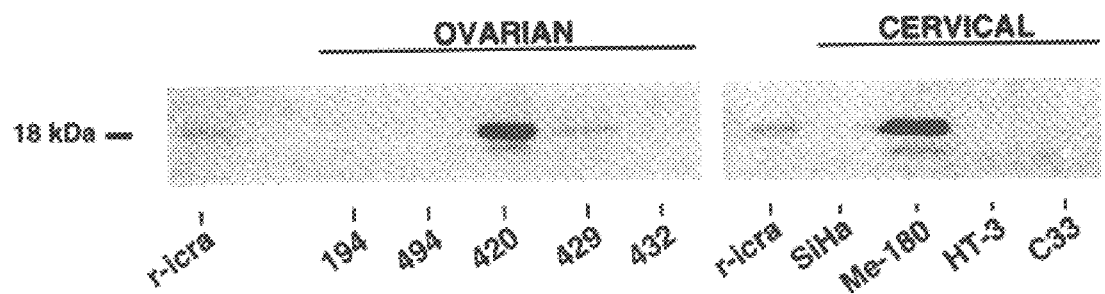
FIG. 3 shows a Western blot analysis of spontaneous expression of icIL-1ra in human ovarian and cervical cancer cell lines, in which cell lysates were harvested from proliferating monolayer cultures, separated by SDS-PAGE, transferred to nitrocellulose, and probed with a polyclonal rabbit anti-human IL-1ra antibody.

The icIL-1ra has been shown to be expressed primarily in cells of epithelial lineage but is inducible in other cell types. As the majority of ovarian malignancies originate from the surface epithelium, icIL-1ra expression was analyzed in 5 human ovarian cancer cell lines. FIG. 3 shows that 2 of 5 ovarian cancer cell lines (OVCA 420 and OVCA 429) spontaneously and constitutively express the 18 kDa icIL-1ra. OVCA 420 cells contained approximately 20 ng icIL-1ra protein/10$^6$ cells while OVCA 429 cells expressed approximately 3–5 ng icIL-1ra protein/10$^6$ cells. Northern analysis and PCR confirmed the presence of mRNA for icIL-1ra in OVCA 420 cells and the absence of icIL-1ra mRNA in OC-194 cells (data not shown). Only one of four cervical cancer cell lines, ME-180, constitutively and spontaneously expressed icIL-1ra (approximately 50–75 ng icIL-1ra protein/10$^6$ cells) (FIG. 3). TCA precipitation of serum-free overnight culture supernatants followed by Western blot analysis revealed that none of the ovarian or cervical cancer cell lines appear to express the secreted form of IL-1ra (data not shown).

EXAMPLE 9 icIL-1ra expression does not block immediate IL-1β signaling

IL-1β has been shown to signal through multiple pathways including the activation of the transcription factor NF-κB. Inactive NF-κB is retained in the cytoplasm by complexing with an inhibitor molecule, IκBα. Upon treatment with various stimuli including IL-1β, IκBα is rapidly phosphorylated and degraded, permitting released NF-κB to translocate to the nucleus and activate gene transcription. The rapid degradation of IκBα can thus be used as a measure of immediate IL-1β signaling. To determine whether expression of icIL-1ra could prevent IκBα degradation, cells were treated with IL-1β for 20 minutes and whole cell lysates were analyzed by Western blotting. Following IL-1β stimulation, IκBα was rapidly degraded with similar kinetics in both OC-194 and OVCA 420 cells (FIG. 4A) and in OVCA 432 and OVCA 429 cells (data not shown). Cytosolic IκBα was not totally replaced in either cell line until approximately 60–90 minutes.

A dose-response curve (FIG. 4B) was used to determine if expression of icIL-1ra altered the dose response to IL-1β. IκBα was not degraded in either cell line when exposed to 1 pg/ml IL-1β. However, IκBα was partially degraded in OC-194 but not OVCA 420 by 10 pg/ml IL-1β. At higher concentrations (>100 pg/ml IL-1), degradation was readily seen in both cell lines and maximal degradation was seen at 1000 pg/ml. These results imply the presence of functional surface IL-1 receptors and suggest that expression of icIL-1ra does not interfere with the initial signaling events mediated through the IL-1 receptor in response to exogenous IL-1β stimulation.

EXAMPLE 10 icIL-1ra expression modulates IL-1β-inducible immediate-early gene expression

Figure 5A:
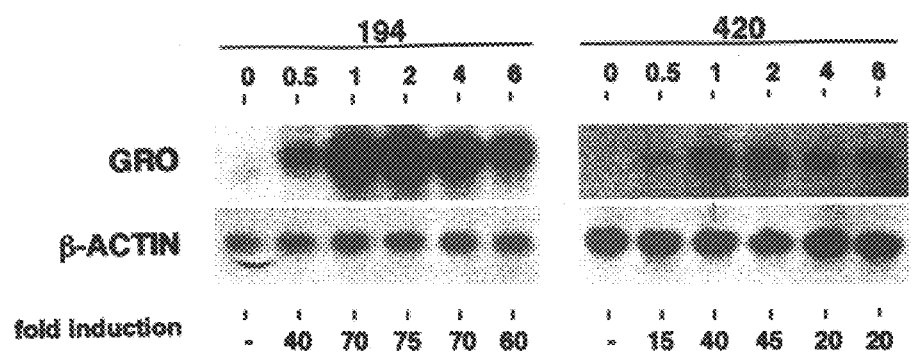
FIG. 5A shows the effect of IL-1β treatment (1 ng/ml for the times indicated) on the expression of GRO mRNA in ovarian cancer cell lines.

IL-1 is a potent inducer of multiple immediate early genes, including the cytokines GRO and IL-8. GRO is often expressed constitutively in normal epithelia but not in malignant carcinomas. However, in both cell types GRO is readily inducible by IL-1. Although expression of icIL-1ra protein does not appear to inhibit immediate IL-1β signaling, we found that cells expressing icIL-1ra display altered mRNA kinetics for genes induced by IL-1. FIG. 5A shows a time course of gene induction for GRO in OC-194 and OVCA 420 cells in response to continuous stimulation with 1 ng/ml IL-1β. Both OC-194 and OVCA 420 cells show a peak increase in GRO mRNA between 1–2 hours. However, following IL-1β treatment, cells which do not express icIL-1ra (OC-194) maintain prolonged expression of GRO mRNA. In contrast to OC-194 cells, the duration of the IL-1-induced expression in OVCA 420 cells was transient, with less than 50% of the induced mRNA remaining 6 hours post-stimulation (FIG. 5A). Analogous to the profile seen for GRO, OC-194 cells displayed similar profiles for other IL-1-inducible genes, such as IL-8 and A20/MAD-6. Peak induction in IL-8 and A20/MAD-6 was seen 1–2 hours post-stimulation, and prolonged expression was detectable at 6 hours (data not shown). The induced expression of IL-8 and A20/MAD-6 in OVCA 420 cells also reflected that seen with GRO, with peak induction detectable 1–2 hours post-stimulation, followed by a rapid loss of the induced mRNA.

Cell lines OVCA 432 (icIL-1ra$^-$) and OVCA 429 (icIL-1ra$^+$) were similarly stimulated with IL-1 and were analyzed for the IL-1-inducible genes GRO and A20/MAD-6. Both cell lines showed peak induction at 1–2 hours. However, unlike the OVCA 432 cells, by 6 hours post-stimulation GRO mRNA had returned to baseline in the OVCA 429 cells. Of all cell lines tested, OVCA 429 was the only one that had expressed GRO mRNA in unstimulated cells.

Figure 5B:
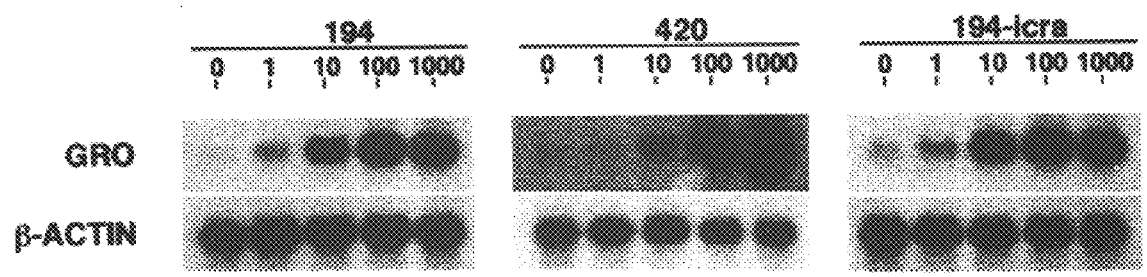
FIG. 5B shows a dose-response curve illustrating the effect of exposure of ovarian cancer cell lines to varying concentrations of IL-1β for 90 minutes on the expression of GRO mRNA.

As the possibility exists that the concentration of IL-1 needed for gene induction differs from that required to degrade IκBα, we performed dose-response curves for GRO induction at a single time point (90 min). Although the response was more vigorous in OC-194 than in OVCA 420 cells, FIG. 5B demonstrates that GRO mRNA could be induced in both cell lines with ≧10 pg/ml IL-1β.

EXAMPLE 11

Modulation of immediate-early gene expression requires continuous exposure to IL-1β

To determine whether icIL-1ra contributed to the observed attenuation of GRO mRNA in IL-1β-stimulated OVCA 420 cells, we designed experiments to evaluate the requirements for maintenance of IL-1β-induced gene expression.

Figure 6A:
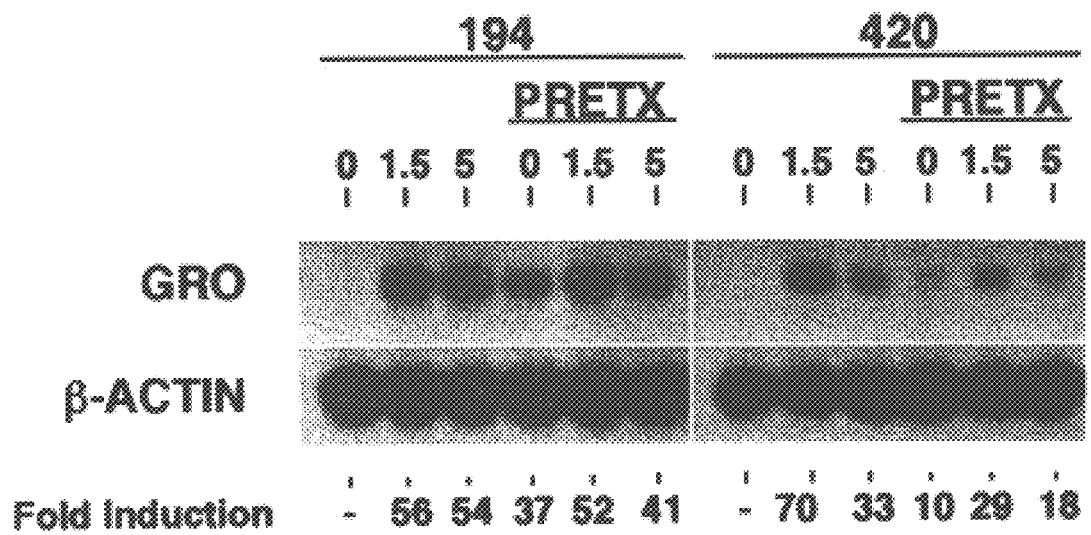
FIG. 6A shows the effect of pretreatment of ovarian cancer cell lines with IL-1β (1 ng/ml for 16 hours) followed by re-exposure to IL-1β (1 ng/ml for the times indicated) on the expression of GRO mRNA.

Continuous, prolonged exposure to IL-1β has been associated with IL-1 receptor desensitization in T cells. To examine the possibility that icIL-1ra may interfere with receptor responses or receptor recycling, we pretreated the ovarian cancer cell lines with 1 ng/ml IL-1β for 16 hours, and then restimulated them with IL-1β for either 90 minutes or 5 hours. Pretreatment of OC-194 cells did not block restimulation of either GRO (FIG. 6A), IL-8 or A20/MAD-6 mRNA (data not shown). Additionally, upon restimulation, the kinetics of mRNAs in the pretreated cells show profiles similar to those in the untreated cells. When compared to the untreated controls, restimulated OC-194 cells achieved mRNA levels comparable to that seen with cells treated with a single exposure to IL-1. Similarly, pretreatment of OVCA 420 cells did not block any restimulation of the IL-1-induced immediate early genes (FIG. 6A). However, the intensity of the induction appears diminished, since restimulation did not lead to mRNA levels similar to those seen initially with a single IL-1 exposure.

Figure 6B:
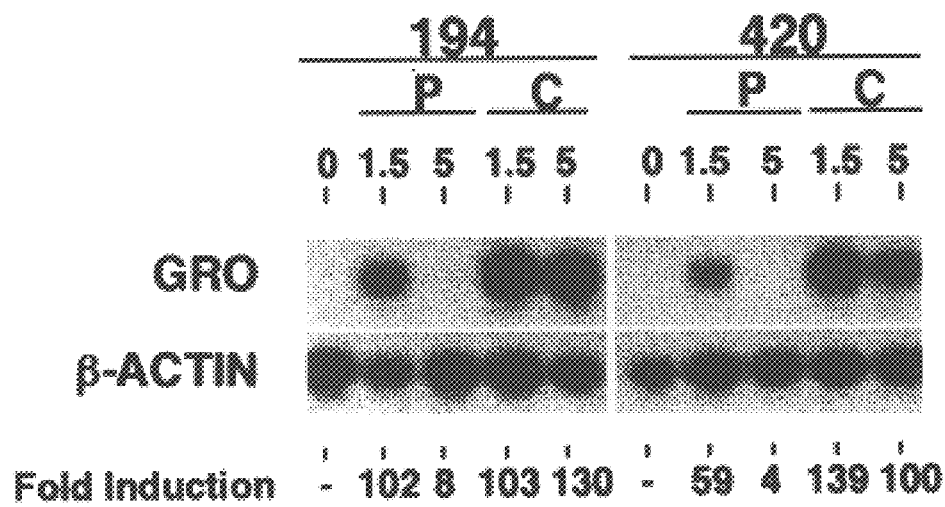
FIG. 6B shows the effect of pulse (1 ng/ml for 10 minutes at 4° C.) or continuous (1 ng/ml continuously) exposure to IL-1β on the expression of GRO mRNA in ovarian cancer cell lines. Fold induction of GRO mRNA over that of unstimulated controls is indicated below the autoradiographs.

To further determine where icIL-1ra might regulate gene induction via continuous restimulation, we incubated the cells with IL-1β for 10 min in the cold to initiate receptor ligation. Subsequently, the IL-1β was removed and the cells were washed extensively in cold PBS and then incubated at 37° C. for either 90 minutes or 5 hours. As seen previously (FIGS. 5A and 6A), in response to continuous exposure to IL-1β the OC-194 cells induced and maintained expression of GRO mRNA while the OVCA 420 cells induced but could not sustain expression (FIG. 6B). In contrast, a pulse exposure to IL-1β resulted in an immediate-early gene expression pattern similar in both icIL-1ra-positive and -negative cells (FIG. 6B). A pulse exposure was sufficient to induce GRO mRNA expression in OC-194 cells. Comparing the fold induction of a pulse IL-1 exposure to a continuous exposure, we found OVCA 420 cells to be less responsive than OC-194 cells. Thus, while a brief exposure to IL-1β can induce GRO mRNA detectable at 90 minutes, such treatment was insufficient to sustain expression. Additionally, these results and those of the pretreatment studies suggest that continuous exposure to IL-1β is required for attenuation of GRO mRNA in icIL-1ra-expressing OVCA 420 cells.

EXAMPLE 12 icIL-1ra expression does not block IL-1β-stimulated transcription

Figure 7:
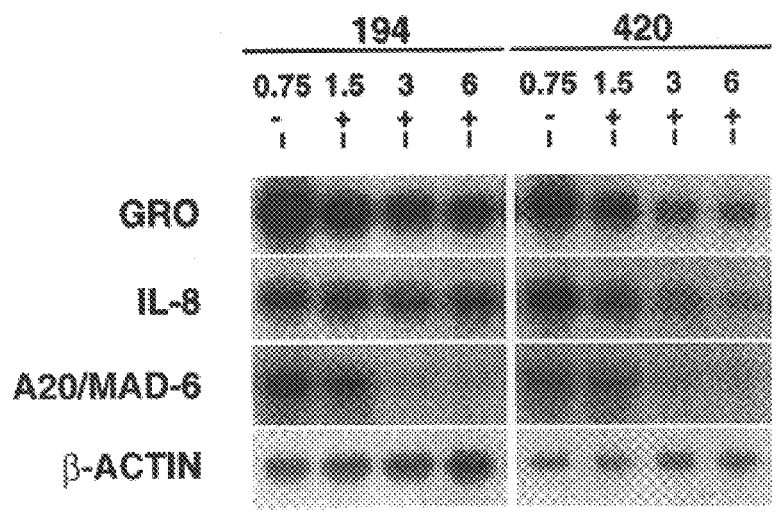
FIG. 7 shows an RNA slot-blot illustrating the effect of exposure to IL-1β (1 ng/ml for the times indicated) on the expression of GRO, IL-8, and A20/MAD-6 mRNA in ovarian cancer cell lines previously exposed to actinomycin-D (5 μg/ml for 45 minutes).

Since continuous IL-1β exposure is required to maintain the induced GRO mRNA levels, the attenuated response seen with OVCA 420 cells may be a result of changes in mRNA stability and/or changes in transcription. Previous studies have demonstrated that GRO mRNA levels can be controlled either at the level of mRNA stability and/or at the level of transcription. To evaluate mRNA stability, we treated IL-1β-stimulated ovarian cancer cells with 5 μg/ml actinomycin-D to block transcription and measured the half-life of GRO mRNA (FIG. 7). In cells which did not express icIL-1ra (OC-194) the half-life of GRO mRNA was approximately 2.9 hours. In contrast, cells expressing icIL-1ra displayed a markedly diminished GRO mRNA half-life of 1.1 hours. The observed half-life effects on GRO mRNA were somewhat specific despite the differences in overall induction. The half-life of A20/MAD-6 mRNA was identical in both OC-194 and OVCA 420 cells, approximately 1.5 hours. It was not possible to determine the half-life of GRO mRNA in unstimulated cells, as no GRO mRNA could be detected in the absence of IL-1 stimulation.

The half-lives of GRO, IL-8 and A20/MAD-6 were measured in additional cell lines after stimulation with IL-1β (data not shown). OVCA 432 resembled OC-194 with a 3.6 hour half-life for GRO mRNA. Both OC-194 and OVCA 432 were found to have half-lives of greater than 6 hours for IL-8. In contrast, in all icIL-1ra+ cell lines, the half-life of GRO mRNA was greater than or equal to 2 hours and 55.1 hours for IL-8. The half-life for IL-1-induced A20/MAD-6 was found to be similar in all cell lines regardless of icIL-1ra status, approximately 1.4–1.8 hours.

Figure 8:
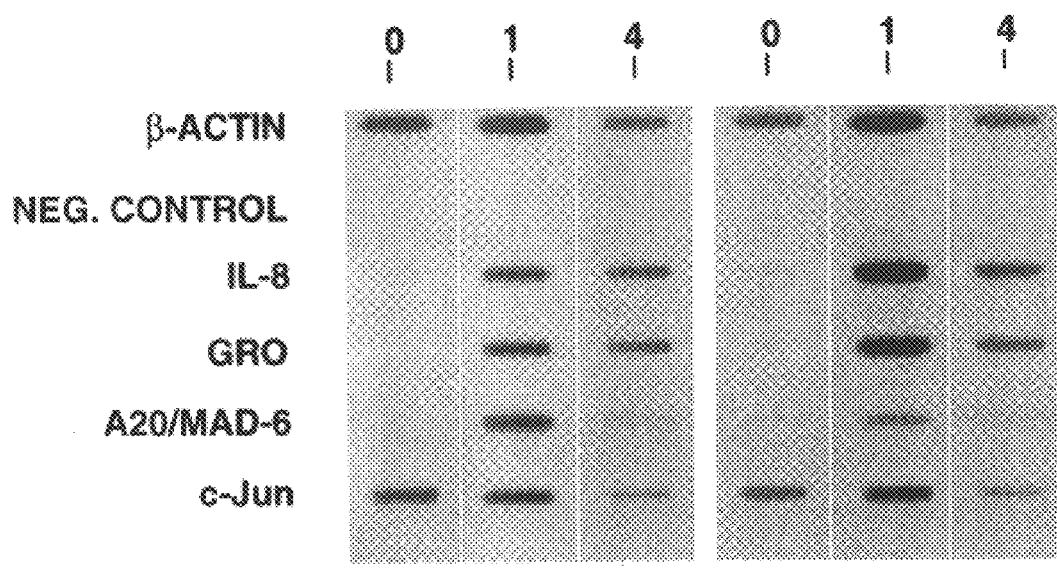
FIG. 8 shows an autoradiograph of nuclear run-on mRNA illustrating the relative transcriptional activation of GRO, IL-8, and A20/MAD-6 in ovarian cancer cell lines exposed to IL-1β (1 ng/ml for 1 or 4 hours).

IL-1β transcriptionally regulates the GRO genes in retinal pigment epithelial cells. We evaluated transcriptional activity in response to IL-1β stimulation by nuclear run-on analysis to determine whether the differences in IL-1-induced GRO mRNA expression were simply reflections of differences in rates of transcription. FIG. 8 shows that GRO, IL-8, and A20/MAD-6 were transcriptionally activated in OC-194 cells following 1 hour of IL-1β stimulation. No transcriptional activity was detected for other cytokine genes including IL-1α, IL-1β, TNF-α, and MIP-1β (data not shown). In OC-194 cells, a 4-hour stimulation with IL-1β resulted in sustained transcriptional activation of GRO and IL-8 (FIG. 8). In contrast, the transcriptional activation for A20/MAD-6 was diminished by 4 hours. IL-1β stimulation induced a similar profile of transcriptional activation at 1 and 4 hours in OVCA 420 cells (FIG. 8). When normalized for actin, the fold induction was less for all genes examined. A 4 h IL-1 stimulation maintained transcription of IL-8 and GRO, but decreased transcriptional activity of A20/MAD-6.

EXAMPLE 13

Retroviral expression of icIL-1ra in OC-194 cells results in an IL-1β-induced immediate-early gene profile analogous to that of OVCA 420 cells.

Figure 9A:
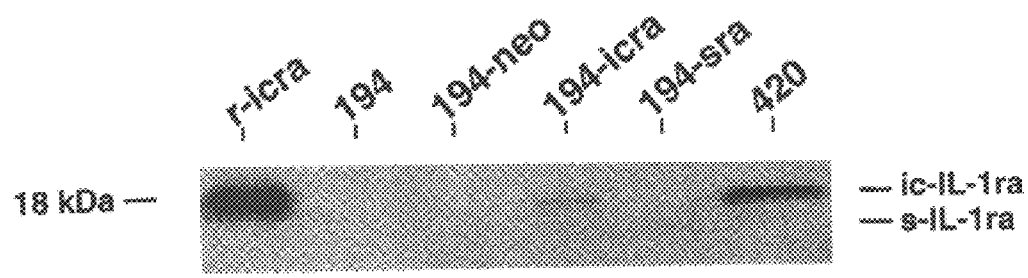
FIG. 9A shows a Western blot analysis of icIL-1ra and sIL-1ra expression in ovarian cancer cell lines stably transfected with an icIL-1ra or sIL-1ra expression vector.

To directly assess the contribution of icIL-1ra to the above observations, we retrovirally transduced icIL-1ra or sIL-1ra into the ovarian cancer cell line OC-194. Following infection and drug selection, we obtained two cell populations that had low but stable expression of icIL-1ra or sIL-1ra protein (FIG. 9A). Approximately 150–200 pg of icIL-1ra protein is expressed per $10^6$ cells. IL-1ra protein was detected in culture supernatants from cells transduced with sIL-1ra (194-sra, <150 pg/ml) but not with the vector alone (194-neo) or with icIL-1ra (194-icra), confirming the specificity and the intracellular location of this protein expression vector.

Figure 4A:
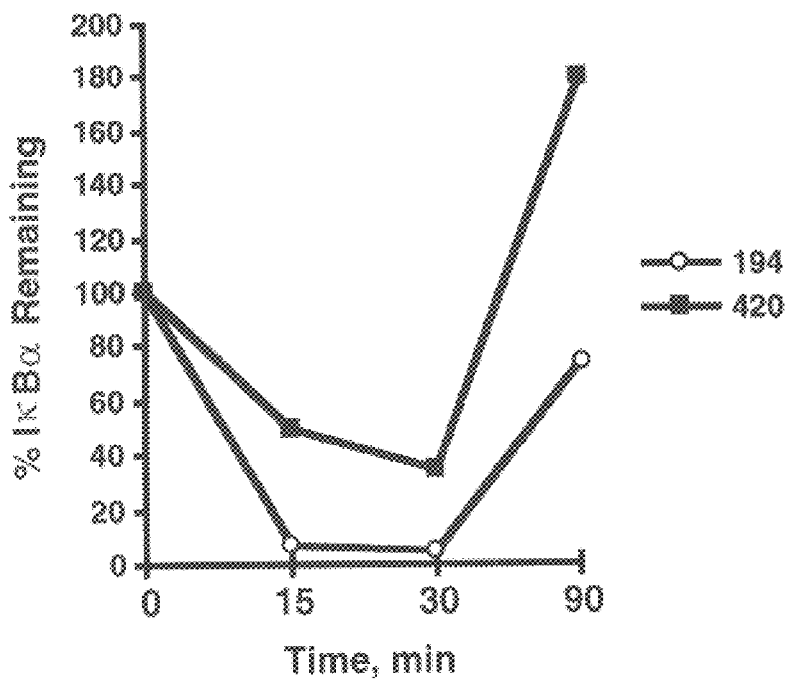
FIG. 4A shows a Western blot illustrating the time-dependent effect of exposure to IL-1β (1 ng/ml) on IκBα degradation in ovarian cancer cell lines.
Figure 4B:
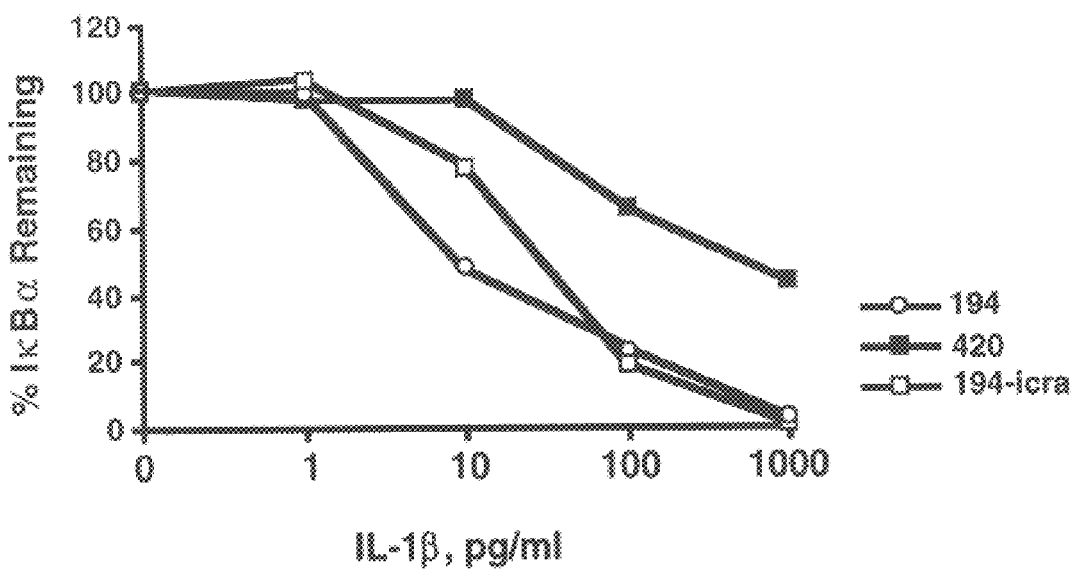
FIG. 4B shows a dose-response curve illustrating the effect of exposure of ovarian cancer cell lines to varying concentrations of IL-1β for 15 minutes.
Figure 4C:
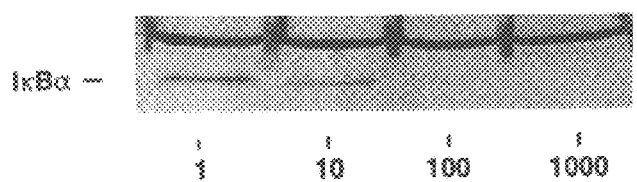
FIG. 4C shows a representative immunoblot for the dose-response experiment illustrated in FIG. 4B.
Figure 9B:
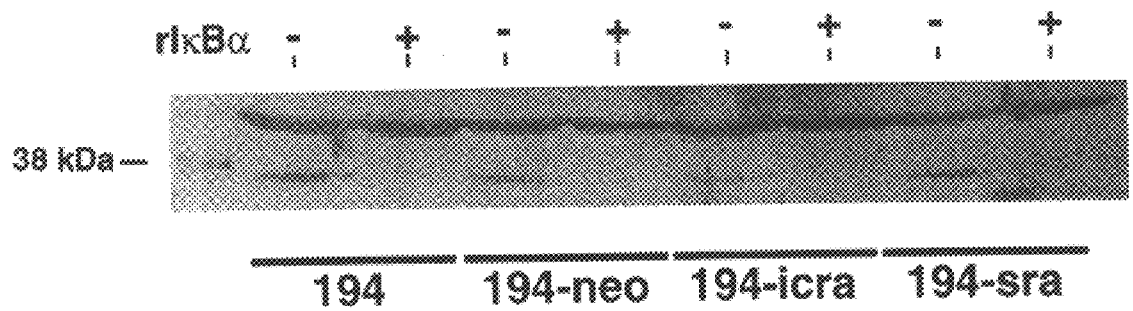
FIG. 9B shows a Western blot analysis illustrating the effect of exposure to IL-1β (1 ng/ml for 20 minutes) on IκBα expression in ovarian cancer cell lines stably transfected with an icIL-1ra or sIL-1ra expression vector.

The retrovirally transduced cells expressing icIL-1ra (194-icra) were found to respond to IL-1β stimulation analogously to icIL-1ra-expressing OVCA 420 cells. As seen with OVCA 420, treatment of infected cells with IL-1β resulted in the rapid degradation of IκBα independent of icIL-1ra expression (FIG. 9B). A dose-response curve showed this degradation to be comparable to that seen with either OC-194 parental cells or OVCA 420 cells (FIG. 4B). Degradation of IκBα was also detected in 194-sra cells treated with IL-1β, suggesting that the level of sIL-1ra produced by these cells is insufficient to block the IL-1 activity used in these experiments. Presumably, the level of sIL-1ra protein achieved over 5 hours was sufficient to compete with IL-1 to block induced gene expression (see below).

Figure 9D:
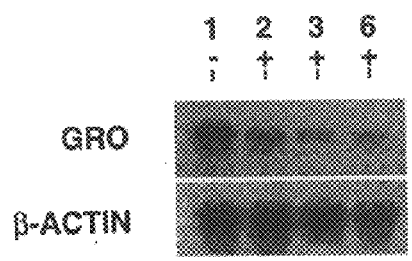
FIG. 9D shows an RNA blot illustrating the effect of exposure to IL-1β (1 ng/ml for the times indicated) on expression of GRO mRNA in 194-icra ovarian cancer cells following a 1 hour exposure to actinomycin-D (5 μg/ml).
Figure 9E:
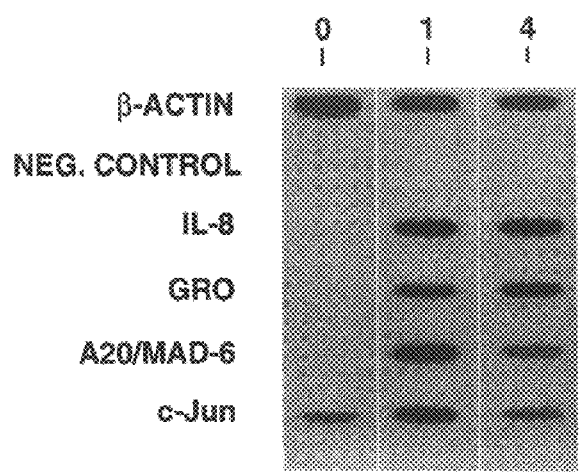
FIG. 9E shows an autoradiograph of GRO, IL-8, and A20/MAD-6 nuclear run-on RNA from 194-icra ovarian cancer cells treated as described in FIG. 9D above.

Stimulation with IL-1β for 90 minutes or 5 hours also resulted in induced mRNA expression patterns (FIG. 9C), analogous to those previously seen with the OVCA 420 cells (FIGS. 5 and 6). Even with a relatively low level of icIL-1ra protein expression, 194-icra cells were incapable of maintaining IL-1-inducible gene expression for GRO, IL-8 and A20/MAD-6 (FIG. 9C). A similar pattern was also seen with 194-sra cells. The inability to maintain IL-1-inducible genes was reflected in the half-lives for GRO, IL-8, and A20/MAD-6 (FIG. 9C). The half-life for GRO was determined to be approximately 1.6 hours, resembling that seen with other icIL-1ra+ cell lines. Nuclear run-on analysis demonstrated IL-1-induced transcriptional activation of all genes examined (FIG. 9E). This profile was analogous to that seen both with the parental OC-194 cells and the OVCA 420 cells (FIG. 8).

The IL-1 receptor antagonist exists in two forms. The secreted form, sIL-1ra, produced by immune cells, is an important regulator of inflammatory responses and functions by competing with the IL-1 ligand for binding to its cognate receptor. The predominantly epithelial cell-associated tissue distribution of the intracellular form, icIL-1ra, suggests a potential for regulation of IL-1 activity at a different level. Although as a purified recombinant protein icIL-1ra can compete with IL-1 for receptor binding, no endogenous biological activity has yet been identified. Here, this study provides the first evidence that icIL-1ra is a unique intracellular inhibitor that has the capacity to alter, by attenuation, IL-1β-inducible immediate-early and recall gene expression without blocking immediate signaling.

Inflammatory cells, such as monocytes and neutrophils, express transcripts for sIL-1ra. While inducible in some cell types, cells of epithelial origin, including normal vaginal and ovarian epithelial cells, spontaneously express icIL-1ra. Here, we demonstrate spontaneous and constitutive expression of icIL-1ra protein in 1 of 4 cervical cancer cell lines and 2 of 5 ovarian cancer cell lines (FIG. 3). The relevance of constitutive icIL-1ra expression in these cells is unknown, but may reflect differences in their respective states of differentiation or in the initial derivation and adaptation of these lines to in vitro culture. None of the tumor cell lines in this study expressed sIL-1ra.

In the normal ovary, IL-1β is important in both stimulating ovulation and initiating subsequent tissue repair with the induced production of hyaluronic acid and proteoglycan synthesis. Ovulation can be blocked by administration of IL-1ra. These and other studies imply that the role of IL-1β in the normal ovary is not to stimulate proliferation per se, but to modulate the immediate cellular environment by altering expression patterns of various ovarian proteins. The data presented herein supports the idea that IL-1 functions by modulating the induction and expression of various molecules, including cytokines. The data further provide evidence of a regulatory protein (icIL-1ra) which limits IL-1 activity in ovarian cancer cells.

Expression of icIL-1ra had no obvious effect on initial IL-1 receptor-mediated responses. The transcription factor NF-κB is an important mediator of IL-1-induced gene transcription. In unstimulated cells, NF-κB is retained in the cytoplasm as an inactive complex bound with its inhibitor IκBα. Following stimulation with IL-1, IκBα is rapidly phosphorylated and degraded, permitting NF-κB translocation to the nucleus and subsequent activation of those genes containing κB enhancer elements. Utilizing the degradation of IκBα as a measure of immediate IL-1β signaling, we observed that IκBα present in unstimulated cells was rapidly degraded within 10 minutes in ovarian cancer cell lines (FIG. 4A). Degradation of IκBα in response to IL-1β stimulation was apparent whether or not icIL-1ra was expressed (FIGS. 4A and 9B). The dose-response kinetics are similar in all cells regardless of icIL-1ra status (FIG. 4B). However, cells that constitutively express icIL-1ra (OVCA 420 and OVCA 429) do not completely degrade IκBα (FIG. 4B and data not shown). Cells engineered to express icIL-1ra degrade IκBα to the same degree as their parental cells (FIGS. 4B and 9B). While the slight shift in responsiveness seen with the OVCA 420 cells may represent a partial block in the signaling pathway, this may be a secondary effect of icIL-1ra expression and one not obtainable with transfection. In addition to the retrovirally infected ovarian cancer cells, we have obtained stable overexpression of icIL-1ra in endometrial stromal cells. While the icIL-1ra level in these cells (up to 20 ng protein/$10^6$ cells) is higher than that obtained with the retroviral vector, the dose-response curves of the stromal cells are identical in the transfected and parental cells. The capacity to signal the degradation of IκBα in response to IL-1β suggests that icIL-1ra expression does not discernibly block immediate signaling through the IL-1 receptor.

Upon degradation of IκBα, NF-κB translocates to the nucleus and participates in the activation of genes containing κB enhancer elements, including those analyzed in the present invention. Following treatment with IL-1β, degradation of IκBα occurred in both OC-194 and OVCA 420 cells, permitting NF-κB activation. Reflective of NF-κB-mediated gene activation, steady-state mRNA levels were induced by IL-1β in a time-dependent manner (FIG. 5). The increase in mRNA transcripts was a consequence of transcriptional activation (FIG. 8). As shown in FIG. 8, GRO, IL-8 and A20/MAD-6 were all transcriptionally induced following exposure to IL-1β. Transcriptional activation was seen in all cell lines examined and occurred independently of icIL-1ra expression (FIGS. 8 and 9D). These data imply that expression of icIL-1ra does not inhibit initial IL-1 responses.

Regulation of IL-1-induced GRO expression occurs by both transcriptional and/or post-transcriptional mechanisms. The data presented in this study indicate that for ovarian cancer cells, both mechanisms appear to regulate GRO expression: IL-1β induced GRO transcription in both OC-194 and OVCA 420 ovarian cancer cells. Induced GRO transcription can be detected 30 minutes following IL-1β treatment (data not shown), and is still detectable at 4 hours post-stimulation (FIGS. 8 and 9C). Expression of icIL-1ra does not appear to affect GRO transcription within this time frame. The icIL-1ra, however, does appear to alter mRNA stability, as both OVCA 420 cells and retrovirally infected 194-icra cells were found to have a shorter IL-1-induced GRO mRNA half-life when compared with OC-194 cells (FIGS. 7 and 9D). The mechanism by which icIL-1ra selectively destabilizes GRO mRNA is currently unknown.

Interestingly, while the levels of IL-1-mediated A20/MAD-6 gene induction varied among the cell lines (data not shown), expression of icIL-1ra did not affect the mRNA stability of A20/MAD-6 (FIG. 7). The apparent lack of changes in A20/MAD6 mRNA stability may be accounted for in that A20/MAD-6 has been shown to be an autoregulated gene, suppressing its own transcription. As presented here, the data suggest multiple pathways of IL-1-inducible gene regulation, only some of which may be regulated by icIL-1ra at the level of attenuating mRNA stability.

The present invention provides evidence that icIL-1ra-expressing cells require continuous exposure to attenuate IL-1-mediated gene induction. Additional evidence that IL-1 responses were attenuated comes from the observation that cells expressing icIL-1ra have a diminished capacity to elicit a long-term or recall response to IL-1 (FIG. 6A). Previously, IL-1 receptors have been shown to become desensitized to IL-1 when continuously exposed to the cytokine. That icIL-1ra-expressing cells have altered IL-1 receptor binding affinities or altered IL-1 receptor trafficking cannot be excluded as possible explanations for this observation. However, using a human T-cell line, it has been concluded that the IL-1 receptor desensitization (i.e., inability to respond to a second IL-1 stimulus) did not result from changes in the numbers or binding affinities of the IL-1 receptor itself, but rather resulted from alterations in an unidentified receptor-proximal transducer. The possibility that icIL-1ra could interfere with the receptor-proximal transducer cannot be excluded from the present observations.

The present invention presents data for the first time identifying a second mechanism for inhibiting IL-1 activity. In the first mechanism, extracellular sIL-1ra inhibits IL-1 by competing directly with the cytokine for binding to the IL-1 receptor. In the second mechanism, intracellular IL-1ra attenuates or destabilizes IL-1-induced mRNAs and thus limits IL-1 responsiveness at a point downstream of the cytokine-receptor interaction.

The epithelial-associated tissue distribution of the intracellular IL-1 receptor antagonist (icIL-1ra) suggests that it functions as a novel regulatory molecule for IL-1. As normal ovarian epithelia express transcripts for icIL-1ra, and as the majority of ovarian cancers arise from the surface epithelia, we examined the role of icIL-1ra in IL-1β-mediated responses in human ovarian cancer cell lines.

We claim:

1. A method for inhibiting a cellular response to interleukin-1 ("IL-1"), comprising:

contacting a mammalian cell that is responsive to interleukin-1 with an intracellular interleukin-1 receptor antagonist ("icIL-1ra") not normally found in said cell.

2. The method of claim 1, wherein said mammalian cell is a human cell.

3. The method of claim 2, wherein said cellular response to IL-1 is adhesion of monocytes.

4. The method of claim 3, wherein said human cell is a human endothelial cell.

5. The method of claim 2, wherein said cellular response to IL-1 is IL-1 dependent IL-2 production.

6. The method of claim 2, wherein said cellular response to IL-1 is IL-1 induced prostaglandin synthesis.

7. The method of claim 5, wherein said human cell is a human fibroblast.

8. The method of claim 7, wherein said prostaglandin is prostaglandin $E_2$.

9. The method of claim 1, 2, 3, 4, 5, 6, 7 or 8 wherein said intracellular interleukin-1 receptor antagonist is the protein of SEQ ID NO: 2.

10. The method of claim 1, 2, 3, 4, 5, 6, 7 or 8 wherein said intracellular interleukin-1 receptor antagonist is a protein encoded by the protein coding region of the DNA of SEQ ID NO: 1.

* * * * *